US012594193B2

(12) United States Patent
Rodrigues

(10) Patent No.: US 12,594,193 B2
(45) Date of Patent: Apr. 7, 2026

(54) SYSTEMS AND METHODS FOR MONITORING OPERATIONAL LIFETIME OF NEGATIVE PRESSURE WOUND TREATMENT APPARATUSES

(71) Applicant: T.J.Smith and Nephew, Limited, Hull (GB)

(72) Inventor: Roberto Damiao Da Costa Rodrigues, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 404 days.

(21) Appl. No.: 17/792,065

(22) PCT Filed: Jan. 6, 2021

(86) PCT No.: PCT/EP2021/050102
§ 371 (c)(1),
(2) Date: Jul. 11, 2022

(87) PCT Pub. No.: WO2021/140107
PCT Pub. Date: Jul. 15, 2021

(65) Prior Publication Data
US 2023/0051967 A1     Feb. 16, 2023

(30) Foreign Application Priority Data
Jan. 9, 2020     (GB) ..................................... 2000274

(51) Int. Cl.
A61F 13/05          (2024.01)
(52) U.S. Cl.
CPC ......... A61F 13/05 (2024.01); *A61M 2205/52* (2013.01)

(58) Field of Classification Search
CPC ..... A61F 13/05; A61M 2205/52; A61M 1/74; A61M 1/96; A61M 1/962; G16H 20/40; G16H 40/06
See application file for complete search history.

(56) References Cited

U.S. PATENT DOCUMENTS 3,810,120 A * 5/1974 Huettner ............. G06F 11/0793
                                                714/E11.003
3,874,387 A     4/1975 Barbieri
                    (Continued)

FOREIGN PATENT DOCUMENTS

CN          201664463 U     12/2010
DE          19844355 A1     4/2000
                    (Continued)

OTHER PUBLICATIONS

International Preliminary Report on Patentability and Written Opinion for Application No. PCT/EP2021/050102, mailed on Jul. 21, 2022, 10 pages.
                    (Continued)

*Primary Examiner* — Kai H Weng
*Assistant Examiner* — Katherine-Ph Minh Pham
(74) *Attorney, Agent, or Firm* — Knobbe, Martens, Olson & Bear, LLP

(57) ABSTRACT

A negative pressure wound therapy system can include a wound dressing configured to be placed over a wound and configured to absorb fluid. The system can include a source of negative pressure configured to generate negative pressure to aspirate fluid from the wound. The system can include a memory. The system can include a controller configured to periodically store a plurality of data sets in the memory, in response to storing a data set of the plurality of data sets at a memory address in the memory, update the memory address for storing a subsequent data set, and in response to determining that the memory address corre-
                    (Continued)

ACTIVATION
910

STANDBY
920

PROVIDE
NEGATIVE
PRESSURE
930

END OF LIFE
940 sponds to a memory address indicative of a duration of time following an initial activation of the system reaching a total permitted operational time of the system, provide an indication that the total permitted operational time of the system has been reached.

21 Claims, 15 Drawing Sheets

(56) References Cited

U.S. PATENT DOCUMENTS

| | | | |
|---|---|---|---|
| 4,224,941 A | 9/1980 | Stivala |
| 4,398,910 A | 8/1983 | Blake et al. |
| 4,534,356 A | 8/1985 | Papadakis |
| 4,569,674 A | 2/1986 | Phillips et al. |
| 4,624,656 A | 11/1986 | Clark et al. |
| 4,681,562 A | 7/1987 | Beck et al. |
| 4,767,943 A | 8/1988 | Adler et al. |
| 4,979,944 A | 12/1990 | Luzsicza |
| 5,055,195 A | 10/1991 | Trasch et al. |
| 5,055,198 A | 10/1991 | Shettigar |
| 5,056,510 A | 10/1991 | Gilman |
| 5,152,757 A | 10/1992 | Eriksson |
| 5,181,905 A | 1/1993 | Flam |
| 5,266,928 A | 11/1993 | Johnson |
| D357,743 S | 4/1995 | Bilitz et al. |
| 5,527,293 A | 6/1996 | Zamierowski |
| 5,549,584 A | 8/1996 | Gross |
| 5,643,189 A | 7/1997 | Masini |
| 5,779,657 A | 7/1998 | Daneshvar |
| 5,833,646 A | 11/1998 | Masini |
| 5,902,256 A | 5/1999 | Benaron |
| 5,964,723 A | 10/1999 | Augustine |
| 6,071,267 A | 6/2000 | Zamierowski |
| 6,142,982 A | 11/2000 | Hunt et al. |
| 6,168,800 B1 | 1/2001 | Dobos et al. |
| 6,183,438 B1 | 2/2001 | Berguer |
| 6,225,523 B1 | 5/2001 | Masini |
| 6,261,276 B1 | 7/2001 | Reitsma |
| 6,261,283 B1 | 7/2001 | Morgan et al. |
| 6,398,767 B1 | 6/2002 | Fleischmann |
| 6,458,109 B1 | 10/2002 | Henley et al. |
| 6,471,982 B1 | 10/2002 | Lydon et al. |
| 6,599,262 B1 | 7/2003 | Masini |
| 6,607,495 B1 | 8/2003 | Skalak et al. |
| 6,685,681 B2 | 2/2004 | Lockwood et al. |
| 6,787,682 B2 | 9/2004 | Gilman |
| 6,794,554 B2 | 9/2004 | Sessions et al. |
| 6,800,074 B2 | 10/2004 | Henley et al. |
| 6,942,633 B2 | 9/2005 | Odland |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,087,806 B2 | 8/2006 | Scheinberg et al. |
| 7,108,683 B2 | 9/2006 | Zamierowski |
| 7,216,651 B2 | 5/2007 | Argenta et al. |
| 7,338,482 B2 | 3/2008 | Lockwood et al. |
| 7,361,184 B2 | 4/2008 | Joshi |
| 7,524,315 B2 | 4/2009 | Blott et al. |
| 7,553,306 B1 | 6/2009 | Hunt et al. |
| 7,611,500 B1 | 11/2009 | Lina et al. |
| 7,615,036 B2 | 11/2009 | Joshi et al. |
| D605,775 S | 12/2009 | Koch et al. |
| D608,007 S | 1/2010 | Arbesman et al. |
| 7,645,253 B2 | 1/2010 | Gura et al. |
| 7,687,678 B2 | 3/2010 | Jacobs |
| 7,776,028 B2 | 8/2010 | Miller et al. |
| 7,779,625 B2 | 8/2010 | Joshi et al. |
| D625,422 S | 10/2010 | Arbesman et al. |
| 7,815,616 B2 | 10/2010 | Boehringer et al. |
| 7,837,673 B2 | 11/2010 | Vogel |
| 7,896,864 B2 | 3/2011 | Lockwood et al. |
| 7,922,676 B2 | 4/2011 | Daskal et al. |
| 7,922,703 B2 | 4/2011 | Riesinger |
| 7,942,866 B2 | 5/2011 | Radl et al. |
| 7,959,624 B2 | 6/2011 | Riesinger |
| 7,976,519 B2 | 7/2011 | Bubb et al. |
| 8,007,257 B2 | 8/2011 | Heaton et al. |
| 8,007,481 B2 | 8/2011 | Schuessler et al. |
| 8,062,272 B2 | 11/2011 | Weston |
| 8,092,441 B2 | 1/2012 | Sugito |
| 8,158,844 B2 | 4/2012 | McNeil |
| 8,167,869 B2 | 5/2012 | Wudyka |
| 8,212,100 B2 | 7/2012 | Moore |
| 8,215,929 B2 | 7/2012 | Shen et al. |
| 8,323,264 B2 | 12/2012 | Weston et al. |
| 8,371,829 B2 | 2/2013 | Jaeb et al. |
| 8,404,921 B2 | 3/2013 | Lee et al. |
| 8,409,160 B2 | 4/2013 | Locke et al. |
| 8,419,696 B2 | 4/2013 | Wilkes |
| 8,425,478 B2 | 4/2013 | Olson |
| 8,439,894 B1 | 5/2013 | Miller |
| 8,449,508 B2 | 5/2013 | Coulthard et al. |
| 8,500,776 B2 | 8/2013 | Ebner |
| 8,529,548 B2 | 9/2013 | Blott et al. |
| 8,545,466 B2 | 10/2013 | Andresen et al. |
| 8,569,566 B2 | 10/2013 | Blott et al. |
| 8,579,872 B2 | 11/2013 | Coulthard et al. |
| 8,603,074 B2 | 12/2013 | Kagan |
| 8,641,691 B2 | 2/2014 | Fink et al. |
| 8,641,693 B2 | 2/2014 | Locke et al. |
| 8,702,665 B2 | 4/2014 | Locke et al. |
| 8,734,425 B2 | 5/2014 | Nicolini |
| 8,795,257 B2 | 8/2014 | Coulthard et al. |
| 8,821,458 B2 | 9/2014 | Locke et al. |
| 8,834,452 B2 | 9/2014 | Hudspeth et al. |
| 8,870,837 B2 | 10/2014 | Locke et al. |
| 8,905,985 B2 | 12/2014 | Allen |
| 8,915,895 B2 | 12/2014 | Jaeb et al. |
| 8,961,496 B2 | 2/2015 | Locke et al. |
| 8,974,429 B2 | 3/2015 | Gordon et al. |
| 9,061,095 B2 | 6/2015 | Adie et al. |
| 9,084,845 B2 | 7/2015 | Adie et al. |
| 9,089,630 B2 | 7/2015 | Perkins et al. |
| 9,198,802 B2 | 12/2015 | Robinson et al. |
| 9,259,558 B2 | 2/2016 | Tsai |
| 9,283,118 B2 | 3/2016 | Locke et al. |
| 9,393,354 B2 | 7/2016 | Freedman et al. |
| 9,414,968 B2 | 8/2016 | Heagle |
| 9,421,133 B2 | 8/2016 | Hu et al. |
| 9,427,505 B2 | 8/2016 | Askem et al. |
| 9,446,176 B2 | 9/2016 | Locke et al. |
| 9,452,088 B2 | 9/2016 | Shulman et al. |
| 9,560,975 B2 | 2/2017 | Mei et al. |
| D787,690 S | 5/2017 | Mackay et al. |
| 9,737,649 B2 | 8/2017 | Begin et al. |
| 9,770,368 B2 | 9/2017 | Robinson et al. |
| 9,814,811 B2 | 11/2017 | Aalders et al. |
| 9,907,703 B2 | 3/2018 | Allen et al. |
| 9,925,092 B2 | 3/2018 | Luckemeyer et al. |
| RE46,778 E | 4/2018 | Peron |
| 9,956,120 B2 | 5/2018 | Locke |
| 10,004,914 B2 | 6/2018 | Nettesheim et al. |
| 10,010,656 B2 | 7/2018 | Jaeb et al. |
| 10,016,309 B2 | 7/2018 | Hartwell |
| 10,016,544 B2 | 7/2018 | Coulthard et al. |
| 10,046,095 B1 | 8/2018 | Middaugh et al. |
| 10,086,117 B2 | 10/2018 | Locke et al. |
| 10,123,909 B2 | 11/2018 | Hartwell |
| 10,201,644 B2 | 2/2019 | Haggstrom et al. |
| 10,265,445 B2 | 4/2019 | Weston |
| 10,384,041 B2 | 8/2019 | Patel et al. |
| 10,463,773 B2 | 11/2019 | Haggstrom et al. |
| 10,660,994 B2 | 5/2020 | Askem et al. |
| 2003/0212357 A1 | 11/2003 | Pace |
| 2004/0076662 A1 | 4/2004 | Riesinger |
| 2004/0087884 A1 | 5/2004 | Haddock et al. |
| 2004/0167482 A1 | 8/2004 | Watson |
| 2005/0012616 A1 | 1/2005 | Forster et al. |
| 2005/0045461 A1 | 3/2005 | Sweetland et al. |

(56) References Cited

U.S. PATENT DOCUMENTS

| | | |
|---|---|---|
| 2005/0065471 A1 | 3/2005 | Kuntz |
| 2005/0119737 A1 | 6/2005 | Bene et al. |
| 2005/0131327 A1 | 6/2005 | Lockwood et al. |
| 2005/0137539 A1 | 6/2005 | Biggie et al. |
| 2006/0029650 A1 | 2/2006 | Coffey |
| 2006/0086598 A1 | 4/2006 | Sneek et al. |
| 2006/0107642 A1 | 5/2006 | Smith et al. |
| 2006/0259102 A1 | 11/2006 | Slatkine |
| 2007/0128055 A1 | 6/2007 | Lee |
| 2007/0179460 A1 | 8/2007 | Adahan |
| 2007/0225663 A1 | 9/2007 | Watt et al. |
| 2007/0255187 A1 | 11/2007 | Branch |
| 2008/0021356 A1 | 1/2008 | Castello Escude et al. |
| 2008/0051716 A1 | 2/2008 | Stutz |
| 2009/0012484 A1 | 1/2009 | Nielsen et al. |
| 2009/0048556 A1 | 2/2009 | Durand |
| 2010/0022990 A1 | 1/2010 | Karpowicz et al. |
| 2010/0100160 A1 | 4/2010 | Edman et al. |
| 2010/0137775 A1 | 6/2010 | Hu et al. |
| 2010/0160881 A1 | 6/2010 | Lin et al. |
| 2010/0280469 A1 | 11/2010 | Hall et al. |
| 2010/0292632 A1 | 11/2010 | Mulvihill et al. |
| 2011/0092927 A1 | 4/2011 | Wilkes et al. |
| 2011/0099338 A1* | 4/2011 | Binz ................ G06F 16/90348 |
| | | 711/E12.001 |
| 2011/0224631 A1 | 9/2011 | Simmons et al. |
| 2011/0292623 A1 | 12/2011 | Stanley |
| 2011/0305736 A1 | 12/2011 | Wieland et al. |
| 2012/0059294 A1 | 3/2012 | Schubert et al. |
| 2012/0109034 A1 | 5/2012 | Locke et al. |
| 2013/0215638 A1 | 8/2013 | Dabov et al. |
| 2014/0100536 A1 | 4/2014 | Angel |
| 2014/0330227 A1 | 11/2014 | Coulthard et al. |
| 2014/0343518 A1 | 11/2014 | Riesinger |
| 2015/0054410 A1* | 2/2015 | Sanders ................ H05B 47/20 |
| | | 315/185 R |
| 2015/0057625 A1 | 2/2015 | Coulthard |
| 2015/0065966 A1* | 3/2015 | Adie ........................ A61M 1/78 |
| | | 604/319 |
| 2015/0174304 A1* | 6/2015 | Askem ................... A61M 1/732 |
| | | 604/319 |
| 2015/0202354 A1 | 7/2015 | Wall |
| 2015/0250931 A1 | 9/2015 | Bharti et al. |
| 2016/0015873 A1 | 1/2016 | Robinson et al. |
| 2016/0166438 A1 | 6/2016 | Rovaniemi |
| 2016/0199546 A1 | 7/2016 | Chao |
| 2016/0206793 A1 | 7/2016 | Robinson et al. |
| 2016/0242964 A1 | 8/2016 | Rapp et al. |
| 2016/0271305 A1 | 9/2016 | Kurihara et al. |
| 2016/0361473 A1 | 12/2016 | Robinson et al. |
| 2017/0112974 A1 | 4/2017 | Fujisaki |
| 2017/0112975 A1 | 4/2017 | Fujisaki |
| 2017/0127525 A1 | 5/2017 | Schonholz |
| 2017/0232189 A1 | 8/2017 | Qin et al. |
| 2017/0296714 A1 | 10/2017 | Locke et al. |
| 2017/0319761 A1 | 11/2017 | Locke et al. |
| 2017/0326277 A1 | 11/2017 | Huang |
| 2017/0368239 A1 | 12/2017 | Askem et al. |
| 2018/0008760 A1 | 1/2018 | Zilbershlag et al. |
| 2018/0021178 A1 | 1/2018 | Locke et al. |
| 2018/0028728 A1 | 2/2018 | Aarestad et al. |
| 2018/0104393 A1 | 4/2018 | Wu et al. |
| 2018/0157803 A1* | 6/2018 | Mirov ................... A61B 5/6849 |
| 2018/0200414 A1 | 7/2018 | Askem et al. |
| 2018/0221547 A1* | 8/2018 | Nicolini ................... A61M 1/80 |
| 2018/0272052 A1 | 9/2018 | Locke et al. |
| 2018/0296397 A1 | 10/2018 | Askem et al. |
| 2018/0308578 A1* | 10/2018 | Armstrong ............. G16H 40/63 |
| 2018/0318137 A1 | 11/2018 | Donda et al. |
| 2018/0318165 A1 | 11/2018 | Donda et al. |
| 2018/0353771 A1 | 12/2018 | Kim et al. |
| 2019/0021911 A1 | 1/2019 | Askem et al. |
| 2019/0125943 A1 | 5/2019 | Askem et al. |
| 2019/0142644 A1 | 5/2019 | Askem et al. |
| 2019/0143007 A1 | 5/2019 | Askem et al. |
| 2019/0159938 A1 | 5/2019 | Askem et al. |
| 2019/0192350 A1 | 6/2019 | Gowans et al. |
| 2019/0282737 A1 | 9/2019 | Beadle et al. |
| 2020/0022846 A1 | 1/2020 | Beadle et al. |
| 2020/0061254 A1 | 2/2020 | Joshi et al. |
| 2021/0001022 A1 | 1/2021 | Lin |

FOREIGN PATENT DOCUMENTS

| | | | |
|---|---|---|---|
| EP | 0512543 | A2 | 11/1992 |
| EP | 1411874 | A1 | 4/2004 |
| EP | 1455701 | B1 | 3/2006 |
| EP | 1448261 | B1 | 2/2007 |
| EP | 1807032 | A1 | 7/2007 |
| EP | 1476217 | B1 | 3/2008 |
| EP | 1931413 | A2 | 6/2008 |
| EP | 1507498 | B1 | 7/2009 |
| EP | 1791579 | B1 | 7/2009 |
| EP | 1947987 | B1 | 5/2010 |
| EP | 1358456 | B1 | 7/2010 |
| EP | 2214728 | A2 | 8/2010 |
| EP | 2254537 | A2 | 12/2010 |
| EP | 2279016 | A1 | 2/2011 |
| EP | 2340064 | A1 | 7/2011 |
| EP | 2344217 | A1 | 7/2011 |
| EP | 2346468 | A2 | 7/2011 |
| EP | 2205190 | B1 | 9/2011 |
| EP | 2370116 | A2 | 10/2011 |
| EP | 2531761 | A1 | 12/2012 |
| EP | 2231088 | B1 | 1/2013 |
| EP | 2015655 | B1 | 3/2013 |
| EP | 2285323 | B1 | 3/2013 |
| EP | 2049055 | B1 | 4/2013 |
| EP | 2440260 | B1 | 5/2013 |
| EP | 2340062 | B1 | 6/2013 |
| EP | 2601984 | A2 | 6/2013 |
| EP | 2603699 | A1 | 6/2013 |
| EP | 1893145 | B1 | 7/2013 |
| EP | 2370142 | B1 | 7/2013 |
| EP | 2279017 | B1 | 8/2013 |
| EP | 2370117 | B1 | 8/2013 |
| EP | 2263742 | B1 | 9/2013 |
| EP | 2659915 | A1 | 11/2013 |
| EP | 1848390 | B1 | 12/2013 |
| EP | 1875081 | B1 | 12/2013 |
| EP | 2271381 | B1 | 12/2013 |
| EP | 2160166 | B1 | 1/2014 |
| EP | 1565219 | B1 | 2/2014 |
| EP | 2305325 | B1 | 4/2014 |
| EP | 2451498 | B1 | 4/2014 |
| EP | 2051675 | B1 | 6/2014 |
| EP | 1485613 | B1 | 7/2014 |
| EP | 1545644 | B1 | 8/2014 |
| EP | 2349154 | B1 | 8/2014 |
| EP | 2146759 | B1 | 9/2014 |
| EP | 2416816 | B1 | 10/2014 |
| EP | 2468323 | B1 | 10/2014 |
| EP | 2658493 | B1 | 10/2014 |
| EP | 1850818 | B1 | 12/2014 |
| EP | 2268348 | B1 | 12/2014 |
| EP | 2561128 | B1 | 1/2015 |
| EP | 2829287 | A1 | 1/2015 |
| EP | 2683285 | B1 | 2/2015 |
| EP | 2470136 | B1 | 3/2015 |
| EP | 2503974 | B1 | 5/2015 |
| EP | 2249894 | B1 | 8/2015 |
| EP | 2802366 | B1 | 8/2015 |
| EP | 2438302 | B1 | 9/2015 |
| EP | 2438301 | B1 | 10/2015 |
| EP | 2802304 | B1 | 12/2015 |
| EP | 2852421 | B1 | 1/2016 |
| EP | 2410962 | B1 | 3/2016 |
| EP | 2640436 | B1 | 3/2016 |
| EP | 2855937 | B1 | 5/2016 |
| EP | 2433594 | B1 | 6/2016 |
| EP | 2919730 | B1 | 6/2016 |
| EP | 2861869 | B1 | 7/2016 |
| EP | 2293749 | B1 | 8/2016 |
| EP | 2305327 | B1 | 10/2016 |

(56) References Cited

FOREIGN PATENT DOCUMENTS

| | | | |
|---|---|---|---|
| EP | 2467086 | B1 | 10/2016 |
| EP | 2470135 | B1 | 10/2016 |
| EP | 2767305 | B1 | 10/2016 |
| EP | 2282788 | B1 | 12/2016 |
| EP | 2462956 | B2 | 3/2017 |
| EP | 3139878 | A1 | 3/2017 |
| EP | 2249761 | B1 | 4/2017 |
| EP | 2968012 | B1 | 4/2017 |
| EP | 1587502 | B1 | 5/2017 |
| EP | 1587554 | B1 | 5/2017 |
| EP | 2731563 | B1 | 5/2017 |
| EP | 2968871 | B1 | 7/2017 |
| EP | 2632613 | B1 | 8/2017 |
| EP | 2888478 | B1 | 8/2017 |
| EP | 2937107 | B1 | 8/2017 |
| EP | 2967627 | B1 | 8/2017 |
| EP | 3139879 | B1 | 8/2017 |
| EP | 2359784 | B1 | 9/2017 |
| EP | 3151795 | B1 | 9/2017 |
| EP | 2367518 | B1 | 10/2017 |
| EP | 3068455 | B1 | 10/2017 |
| EP | 2558046 | B2 | 11/2017 |
| EP | 2736548 | B1 | 11/2017 |
| EP | 3052158 | B1 | 11/2017 |
| EP | 3257486 | A1 | 12/2017 |
| EP | 2593058 | B1 | 3/2018 |
| EP | 3092988 | B1 | 3/2018 |
| EP | 3139880 | B1 | 3/2018 |
| EP | 2868300 | B1 | 6/2018 |
| EP | 1496822 | B1 | 8/2018 |
| EP | 2879633 | B1 | 8/2018 |
| EP | 2227203 | B1 | 9/2018 |
| EP | 3106186 | B1 | 9/2018 |
| EP | 3162330 | B1 | 9/2018 |
| EP | 3169382 | B1 | 9/2018 |
| EP | 3203953 | B1 | 9/2018 |
| EP | 2941280 | B1 | 10/2018 |
| EP | 3244852 | B1 | 10/2018 |
| EP | 2687241 | B2 | 11/2018 |
| EP | 2974754 | B1 | 11/2018 |
| EP | 3062753 | B1 | 11/2018 |
| EP | 3120879 | B1 | 12/2018 |
| EP | 3191149 | B1 | 1/2019 |
| EP | 2370130 | B1 | 3/2019 |
| EP | 3053609 | B1 | 3/2019 |
| EP | 3180048 | B1 | 3/2019 |
| EP | 3143974 | B1 | 4/2019 |
| EP | 2285432 | B2 | 6/2019 |
| EP | 3187209 | B1 | 6/2019 |
| EP | 2740501 | B1 | 7/2019 |
| EP | 3050545 | B1 | 7/2019 |
| EP | 3311856 | B1 | 7/2019 |
| EP | 3319656 | B1 | 8/2019 |
| EP | 2355762 | B1 | 9/2019 |
| EP | 2822613 | B1 | 9/2019 |
| EP | 2863855 | B1 | 9/2019 |
| EP | 2482912 | B1 | 10/2019 |
| EP | 3038667 | B1 | 10/2019 |
| EP | 3129095 | B1 | 10/2019 |
| EP | 3191150 | B1 | 10/2019 |
| EP | 3280466 | B1 | 10/2019 |
| EP | 3287113 | B1 | 10/2019 |
| EP | 3281650 | B1 | 11/2019 |
| EP | 2244756 | B1 | 12/2019 |
| EP | 2968702 | B1 | 12/2019 |
| FR | 2939320 | A1 | 6/2010 |
| GB | 2511523 | A | 9/2014 |
| JP | H04354722 | A | 12/1992 |
| RU | 131622 | U1 | 8/2013 |
| WO | WO-2009098696 | A2 | 8/2009 |
| WO | WO-2009120951 | A2 | 10/2009 |
| WO | WO-2011135285 | A1 | 11/2011 |
| WO | WO-2011144888 | A1 | 11/2011 |
| WO | WO-2014099709 | A1 | 6/2014 |
| WO | WO-2016126560 | A1 | 8/2016 |
| WO | WO-2017062042 | A1 | 4/2017 |
| WO | WO-2017079174 | A1 | 5/2017 |
| WO | WO-2017196888 | A1 | 11/2017 |
| WO | WO-2018041854 | A1 | 3/2018 |
| WO | WO-2018056060 | A1 | 3/2018 |
| WO | WO-2018096390 | A1 | 5/2018 |
| WO | WO-2018115461 | A1 | 6/2018 |
| WO | WO-2018156730 | A1 | 8/2018 |
| WO | WO-2018158250 | A1 | 9/2018 |
| WO | WO-2018162613 | A1 | 9/2018 |
| WO | WO-2018164803 | A1 | 9/2018 |
| WO | WO-2018185138 | A1 | 10/2018 |
| WO | WO-2018192978 | A1 | 10/2018 |
| WO | WO-2018206420 | A1 | 11/2018 |
| WO | WO-2019048638 | A1 | 3/2019 |
| WO | WO-2019053101 | A1 | 3/2019 |
| WO | WO-2019053106 | A1 | 3/2019 |
| WO | WO-2019086332 | A1 | 5/2019 |
| WO | WO-2019086341 | A1 | 5/2019 |
| WO | WO-2019086475 | A1 | 5/2019 |
| WO | WO-2019152140 | A1 | 8/2019 |
| WO | WO-2019193141 | A1 | 10/2019 |
| WO | WO-2020005577 | A1 | 1/2020 |
| WO | WO-2020110626 | A1 | 6/2020 |

OTHER PUBLICATIONS

International Search Report and Written Opinion for Application No. PCT/EP2021/050102, mailed on May 6, 2021, 16 pages.
Wikipedia, "VxWorks—Wikipedia", Aug. 17, 2019, 14 pages, retrieved from the Internet: URL: https://web.archive.org/web/20190817134104/https://en.wikipedia.org/wiki/VxWorks.

* cited by examiner

SYSTEMS AND METHODS FOR MONITORING OPERATIONAL LIFETIME OF NEGATIVE PRESSURE WOUND TREATMENT APPARATUSES

CROSS-REFERENCE TO RELATED APPLICATIONS

This application is a U.S. national stage application of International Patent Application No. PCT/EP2021/050102, filed Jan. 6, 2021, which claims priority to U.K. Patent Application No. 2000274.7, filed on Jan. 9, 2020, the disclosure of each of which is hereby incorporated by reference in its entirety.

TECHNICAL FIELD

Embodiments described herein relate to apparatuses, systems, and methods the treatment of wounds, for example using dressings in combination with negative pressure wound therapy.

DESCRIPTION OF THE RELATED ART

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

SUMMARY

A negative pressure wound therapy system can include a wound dressing configured to be placed over a wound of a patient. The wound dressing can be configured to absorb fluid. The system can include a source of negative pressure configured to generate negative pressure to aspirate fluid from the wound. The system can include a memory. The system can include a controller configured to periodically store a plurality of data sets in the memory. The controller can be configured to, in response to storing a data set of the plurality of data sets at a memory address in the memory, update the memory address for storing a subsequent data set. The controller can be configured to, in response to determining that the memory address corresponds to a memory address indicative of a duration of time following an initial activation of the system reaching a total permitted operational time of the system, provide an indication that the total permitted operational time of the system has been reached.

The system of any of the preceding paragraphs and/or any of the systems disclosed herein can include one or more of the following features. Controller can be configured to store each data set of the plurality of data sets at an expiration of a time interval. Time interval can be fixed. Data sets can be of a fixed size. Controller can be configured increment the memory address by a size of the data set. Memory address indicative of the duration of time reaching the total permitted operational time of the system can be determined based on one or more of a frequency of storing the data sets in the memory, size of the data sets, and the total permitted operational time of the system. Memory address indicative of the duration of time reaching the total permitted operational time of the system can be determined by multiplying the frequency of storing the data sets in the memory by the size of the data sets and the total permitted operational time of the system. Memory address indicative of the duration of time reaching the total permitted operational time of the system can be further determined based on a size of data configured to be stored at the memory address.

The system of any of the preceding paragraphs and/or any of the systems disclosed herein can include one or more of the following features. Permitted total operational time of the system can be 7 days, 10 days, or 14 days. Plurality of data sets can include data related to provision of negative pressure therapy. Indication that the total permitted operational time of the system has been reached can include disabling generation of negative pressure by the source of negative pressure. Memory can be nonvolatile memory. The system can include a power source configured to power at least one of the source of negative pressure, the memory, and the controller. At least one of the source of negative pressure, the memory, the controller, or the power source is disposed on or within the wound dressing.

A method of operating the system of any of the preceding paragraphs and/or any of the systems disclosed herein is disclosed.

A method of operating a negative pressure wound therapy system can include, by a controller of the negative pressure wound therapy system, periodically storing a plurality of data sets in a memory of the negative pressure wound therapy system. The method can include in response to storing a data set of the plurality of data sets at a memory address in a memory of negative pressure wound therapy system, updating the memory address for storing a subsequent data set. The method can include in response to determining that the memory address corresponds to a memory address indicative of a duration of time following an initial activation of the system reaching a total permitted operational time of the system, providing an indication that the total permitted operational time of the system has been reached.

The method of any of the preceding paragraphs and/or any of the methods disclosed herein can include one or more of the following features. The method can include storing each data set of the plurality of data sets at an expiration of a time interval. Time interval can be fixed. Data sets can be of a fixed size. The method can include incrementing the memory address by a size of the data set. Memory address indicative of the duration of time reaching the total permitted operational time of the system can be determined based on a frequency of storing the data sets in the memory, size of the data sets, and the total permitted operational time of the system. Memory address indicative of the duration of time reaching the total permitted operational time of the system can be determined by multiplying the frequency of storing the data sets in the memory by the size of the data sets and the total permitted operational time of the system. Memory address indicative of the duration of time reaching the total permitted operational time of the system can be determined based on a size of data configured to be stored at the memory address. Total permitted operational time of the system can be 7 days, 10 days, or 14 days. Plurality of data sets can include data related to provision of negative pressure therapy. The indication that the total permitted operational time of the system has been reached can include disabling generation of negative pressure by a source of negative pressure of the negative pressure wound therapy system. The memory can be nonvolatile memory.

A non-transitory computer readable medium can store instructions that, when executed by a controller of a negative pressure of the negative pressure wound therapy system, can cause the controller to perform the method of any of the preceding paragraphs and/or any of the methods disclosed herein.

DETAILED DESCRIPTION

Figure 1A:
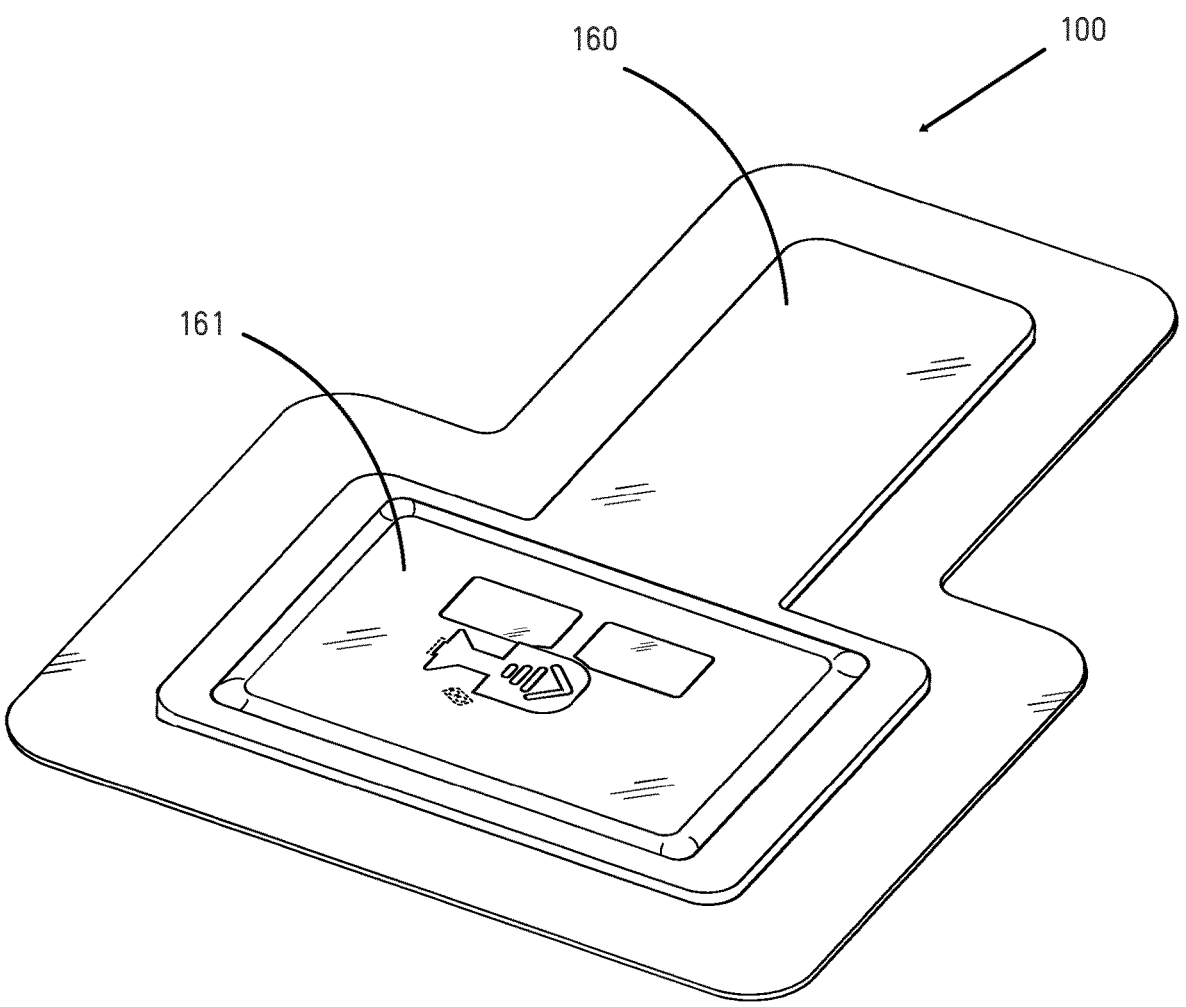
FIGS. 1A-1C illustrate a wound dressing incorporating a source of negative pressure and/or other electronic components within the wound dressing.

Embodiments disclosed herein relate to apparatuses and methods of treating a wound with reduced pressure, including a source of negative pressure and wound dressing components and apparatuses. These apparatuses and components, including but not limited to wound overlays, backing layers, cover layers, drapes, sealing layers, spacer layers, absorbent layers, transmission layers, wound contact layers, packing materials, fillers and/or fluidic connectors are sometimes collectively referred to herein as dressings.

It will be appreciated that throughout this specification reference is made to a wound. It is to be understood that the term wound is to be broadly construed and encompasses open and closed wounds in which skin may be torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

It will be understood that embodiments of the present disclosure are generally applicable to use in NPWT or topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as $-X$ mmHg, represent pressure levels relative to normal ambient atmospheric pressure, which can correspond to 760 mmHg (or 1 atm, 29.93 inHg, 101.325 kPa, 14.696 psi, 1013.25 mbar, etc.). Accordingly, a negative pressure value of $-X$ mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (such as, $-40$ mmHg is less than $-60$ mmHg). Negative pressure that is "more" or "greater" than $-X$ mmHg corresponds to pressure that is further from atmospheric pressure (such as, $-80$ mmHg is more than $-60$ mmHg). In some cases, local ambient atmospheric pressure is used as a reference point, and such local atmospheric pressure may not necessarily be, for example, 760 mmHg.

The negative pressure range can be approximately $-80$ mmHg, or between about $-20$ mmHg and $-200$ mmHg. Note that these pressures are relative to normal ambient atmospheric pressure, which can be 760 mmHg. Thus, $-200$ mmHg would be about 560 mmHg in practical terms. In some cases, the pressure range can be between about $-40$ mmHg and $-150$ mmHg. Alternatively, a pressure range of up to $-75$ mmHg, up to $-80$ mmHg or over $-80$ mmHg can be used. Also in some cases a pressure range of below $-75$ mmHg can be used. Alternatively, a pressure range of over approximately $-100$ mmHg, or even $-150$ mmHg, can be supplied by the negative pressure apparatus.

Wound Dressing

Figure 1B:
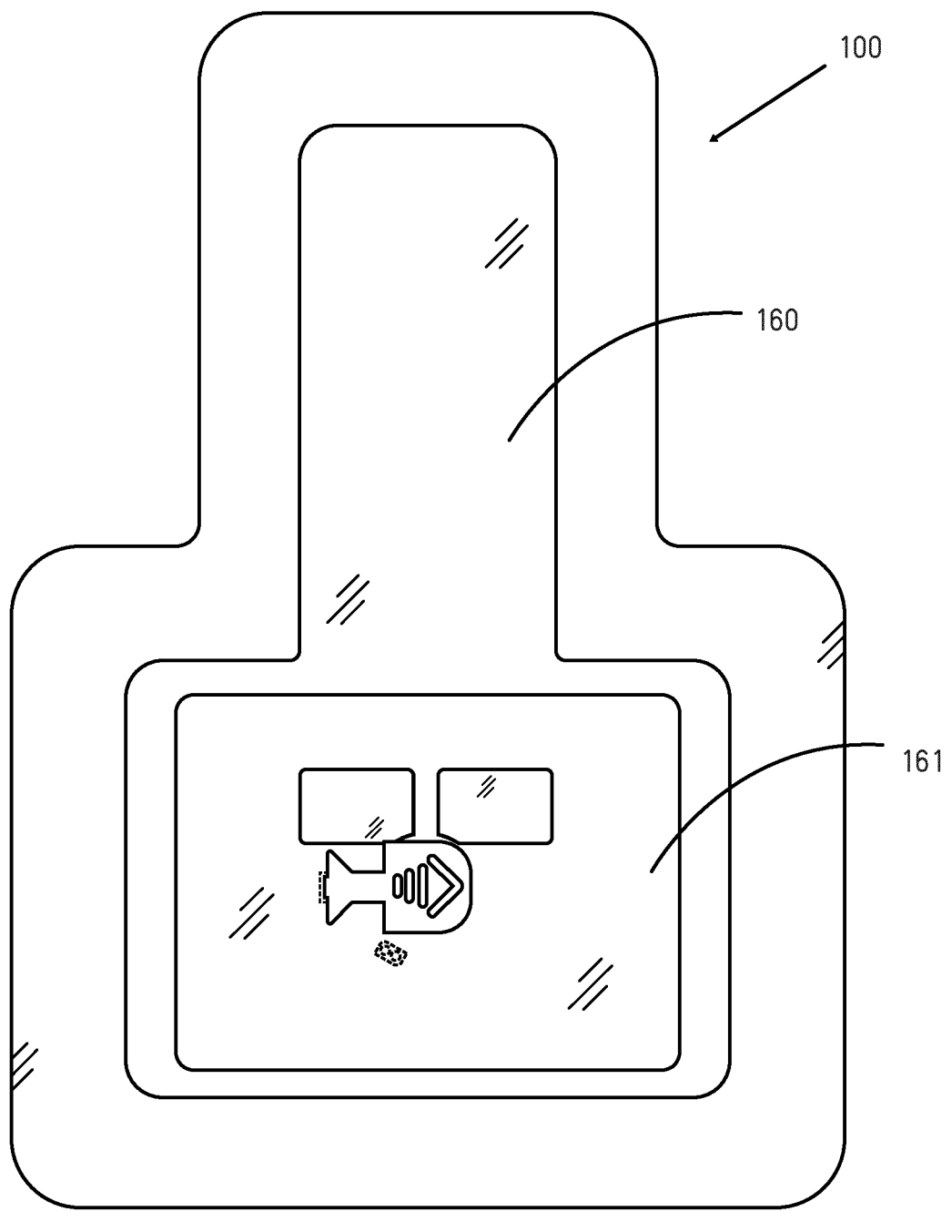
Figure 1C:
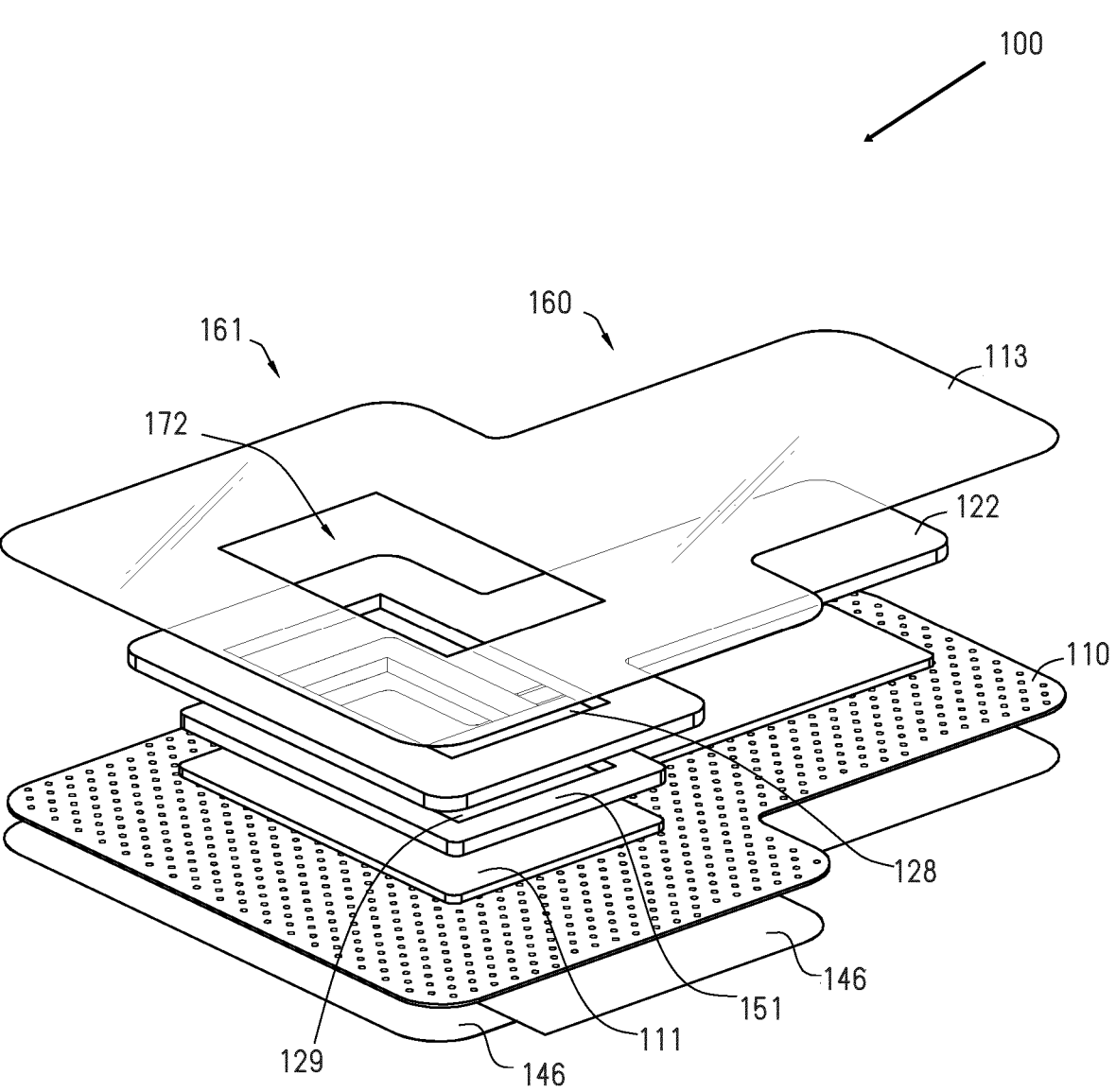

A source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. The material layers can include a wound contact layer, one or more absorbent layers, one or more transmission or spacer layers, and a backing layer or cover layer covering the one or more absorbent and transmission or spacer layers. The wound dressing can be placed over a wound and sealed to the wound with the pump and/or other electronic components contained under the cover layer within the wound dressing. The dressing can be provided as a single article with all wound dressing elements (including the pump) pre-attached and integrated into a single unit. A periphery of the wound contact layer can be attached to the periphery of the cover layer enclosing all wound dressing elements as illustrated in FIG. 1A-1C.

The pump and/or other electronic components can be configured to be positioned adjacent to or next to the absorbent and/or transmission layers so that the pump and/or other electronic components are still part of a single article to be applied to a patient. The pump and/or other electronics can be positioned away from the wound site. Although certain features disclosed herein may be described as relating to systems and method for controlling operation of a negative pressure wound therapy system in which the pump and/or other electronic components are positioned in or on the wound dressing, the systems and methods disclosed herein are applicable to any negative pressure wound therapy system or any medical device. FIGS. 1A-1C illustrate a wound dressing incorporating the source of negative pressure and/or other electronic components within the wound dressing. FIGS. 1A-1C illustrate a wound dressing 100 with the pump and/or other electronics positioned away from the wound site. The wound dressing can include an electronics area 161 and an absorbent area 160. The dressing can comprise a wound contact layer 110 (not shown in FIGS. 1A-1B) and a moisture vapor permeable film, cover layer or backing layer 113 positioned above the contact layer and other layers of the dressing. The wound dressing layers and components of the electronics area as well as the absorbent area can be covered by one continuous cover layer 113 as shown in FIGS. 1A-1C.

A layer 111 of porous material can be located above the wound contact layer 110. As used herein, the terms porous material, spacer, and/or transmission layer can be used interchangeably to refer to the layer of material in the dressing configured to distribute negative pressure throughout the wound area. This porous layer, or transmission layer, 111 allows transmission of fluid including liquid and gas away from a wound site into upper layers of the wound dressing. In particular, the transmission layer 111 preferably ensures that an open air channel can be maintained to communicate negative pressure over the wound area even when the absorbent layer has absorbed substantial amounts of exudates. The layer 111 should preferably remain open under the typical pressures that will be applied during negative pressure wound therapy as described above, so that the whole wound site sees an equalized negative pressure. The layer 111 may be formed of a material having a three dimensional structure. For example, a knitted or woven spacer fabric (for example Baltex 7970 weft knitted polyester) or a non-woven fabric could be used.

Further, one or more absorbent layers (such as layers 122, 151) for absorbing and retaining exudate aspirated from the wound can be utilized. A superabsorbent material can be used in the absorbent layers 122, 151. The one or more layers 122, 151 of absorbent material may be provided above the transmission layer 111. Since in use each of the absorbent layers experiences negative pressures, the material of the absorbent layer can be chosen to absorb liquid under such circumstances. The absorbent layers 122. 151 may comprise a composite comprising superabsorbent powder, fibrous material such as cellulose, and bonding fibers. The composite can be an airlaid, thermally-bonded composite.

The electronics area 161 can include a source of negative pressure (such as a pump) and some or all other components of the TNP system, such as power source(s), sensor(s), connector(s), user interface component(s) (such as button(s), switch(es), speaker(s), screen(s), etc.) and the like, that can be integral with the wound dressing. For example, the electronics area 161 can include a button or switch 114 as shown in FIGS. 1A-1B. The button or switch 114 can be used for operating the pump (such as, turning the pump on/off).

The electronics area 161 of the dressing can comprise one or more layers of transmission or spacer material and/or absorbent material and electronic components can be embedded within the one or more layers of transmission or spacer material and/or absorbent material. The layers of transmission or absorbent material can have recesses or cut outs to embed the electronic components within whilst providing structure to prevent collapse. As shown in FIG. 1C, recesses 128 and 129 can be provided in absorbent layers 151 and 122, respectively.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound. Additionally, the layers can have a proximal wound-facing face referring to a side or face of the layer closest to the skin or wound and a distal face referring to a side or face of the layer furthest from the skin or wound.

The cover layer may include a cutout 172 positioned over at least a portion of the aperture 128 in the absorbent layer 122 to allow access and fluid communication to at least a portion of the absorbent layers 122 and 151, transmission layer 111, and would contact layer 110 positioned below. An electronics assembly such as described below can be positioned in the apertures 128, 129, and 172 of the first and second absorbent material 151 and 122 and the cover layer 113. The electronics assembly can include a pump, power source, and a printed circuit board as described with reference to FIGS. 3 and 4A-4B.

Before use, the dressing can include one or more delivery layers 146 adhered to the bottom surface of the wound contact layer. The delivery layer 146 can cover adhesive or apertures on the bottom surface of the wound contact layer 110. The delivery layer 146 can provided support for the dressing and can assist in sterile and appropriate placement of the dressing over the wound and skin of the patient. The delivery layer 146 can include handles that can be used by the user to separate the delivery layer 146 from the wound contact layer 110 before applying the dressing to a wound and skin of a patient.

Electronics Assembly Incorporated Within the Wound Dressing

Figures 2A, 2B:
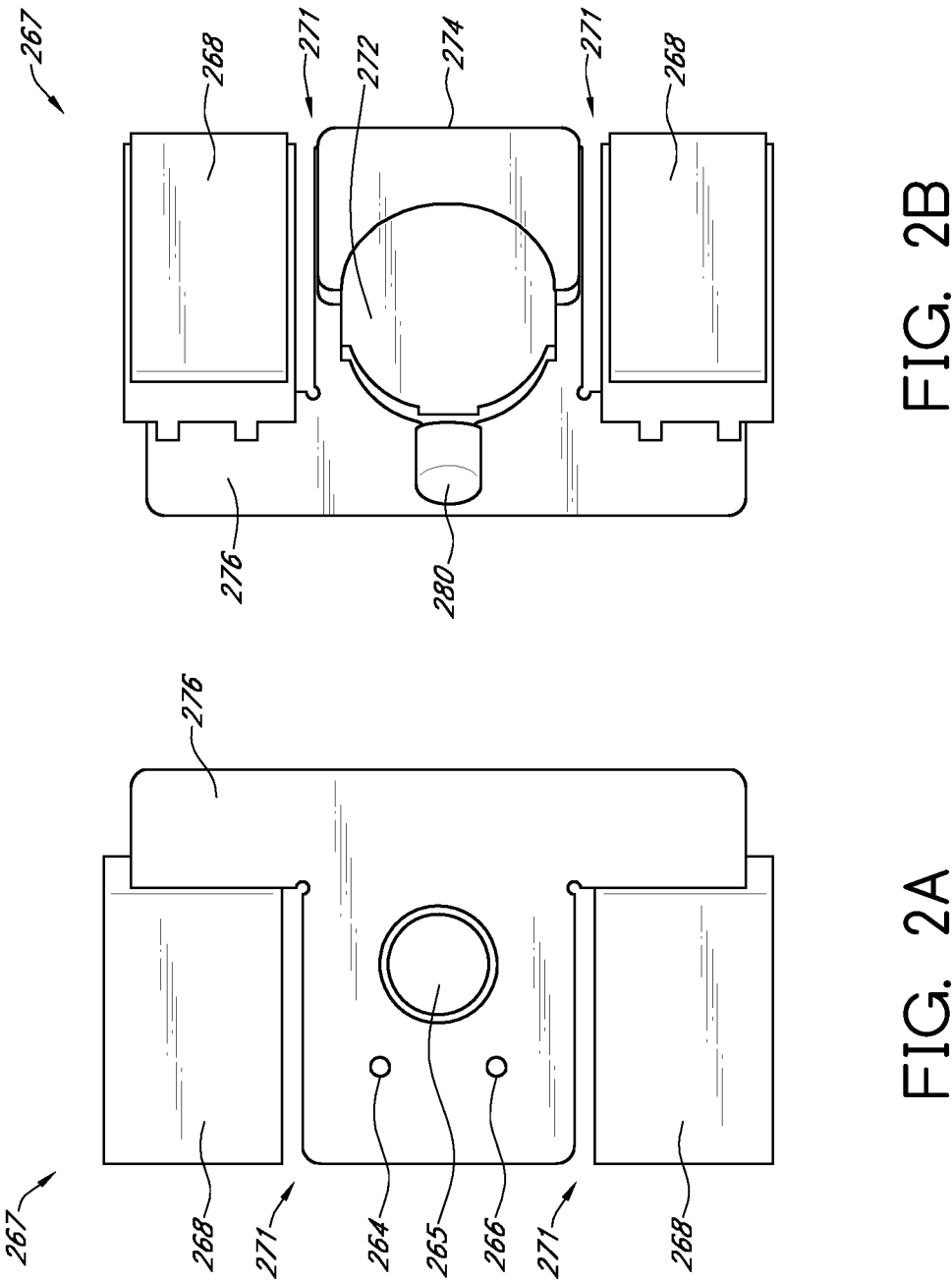
FIGS. 2A-2B illustrate an electronics unit that may be incorporated into a wound dressing.

FIGS. 2A-2B illustrate an electronics unit 267 that can be incorporated into a wound dressing. FIG. 2A illustrates the top view of the electronics unit. FIG. 2B illustrates a bottom or wound facing surface of the electronics unit. The electronics unit 267 can include a pump 272 and one or more power sources 268, such as batteries. The electronics unit 267 can include a circuit board 276 configured to be in electrical communication with the pump 272 and/or power source 268. The circuit board 276 can be flexible or substantially flexible.

As illustrated in FIG. 2A, the electronics unit 267 can include single button or switch 265 on the upper surface of the unit. The single button or switch 265 can be used as an on/off button or switch to stop and start operation of the pump and/or electronic components. The electronics unit 267 can also include one or more vents or exhaust apertures 264 on the circuit board 276 for expelling the air exhausted from the pump. As shown in FIG. 2B, a pump outlet exhaust mechanism 274 (sometimes referred to as pump exhaust mechanism or pump outlet mechanism) can be attached to the outlet of the pump 272.

The electronics unit 267 can include a pump inlet protection mechanism 280 as shown in FIG. 2B positioned on the portion of the electronics unit closest to the absorbent area and aligned with the inlet of the pump 272. The pump inlet protection mechanism 280 is positioned between the pump inlet and the absorbent area or absorbent layer of the dressing. The pump inlet protection mechanism 280 can include hydrophobic material to prevent fluid from entering the pump 272. The pump inlet protection mechanism 280 (or any of the inlet protection mechanisms disclosed herein) can include a filter.

The upper surface of the electronics unit 267 can include one or more indicators 266 for indicating a condition of the pump and/or level of pressure within the dressing. The indicators can be small LED lights or other light source that are visible through the dressing components or through holes in the dressing components above the indicators. The indicators can be green, yellow, red, orange, or any other color. For example, there can be two lights, one green light and one orange light. The green light can indicate the device is working properly and the orange light can indicate that there is some issue with the pump (such as, leak, saturation level of the dressing, blockage downstream of the pump, exhaust blockage, low battery, or the like).

The power source 268 can be in electrical communication with the circuit board 276. One or more power source connections are connected to a surface of the circuit board 276. The circuit board 276 can have other electronics incorporated within. For example, the circuit board 276 may support various sensors including, but not limited to, one or more pressure sensors, temperature sensors, optic sensors and/or cameras, and/or saturation indicators.

Figure 3:
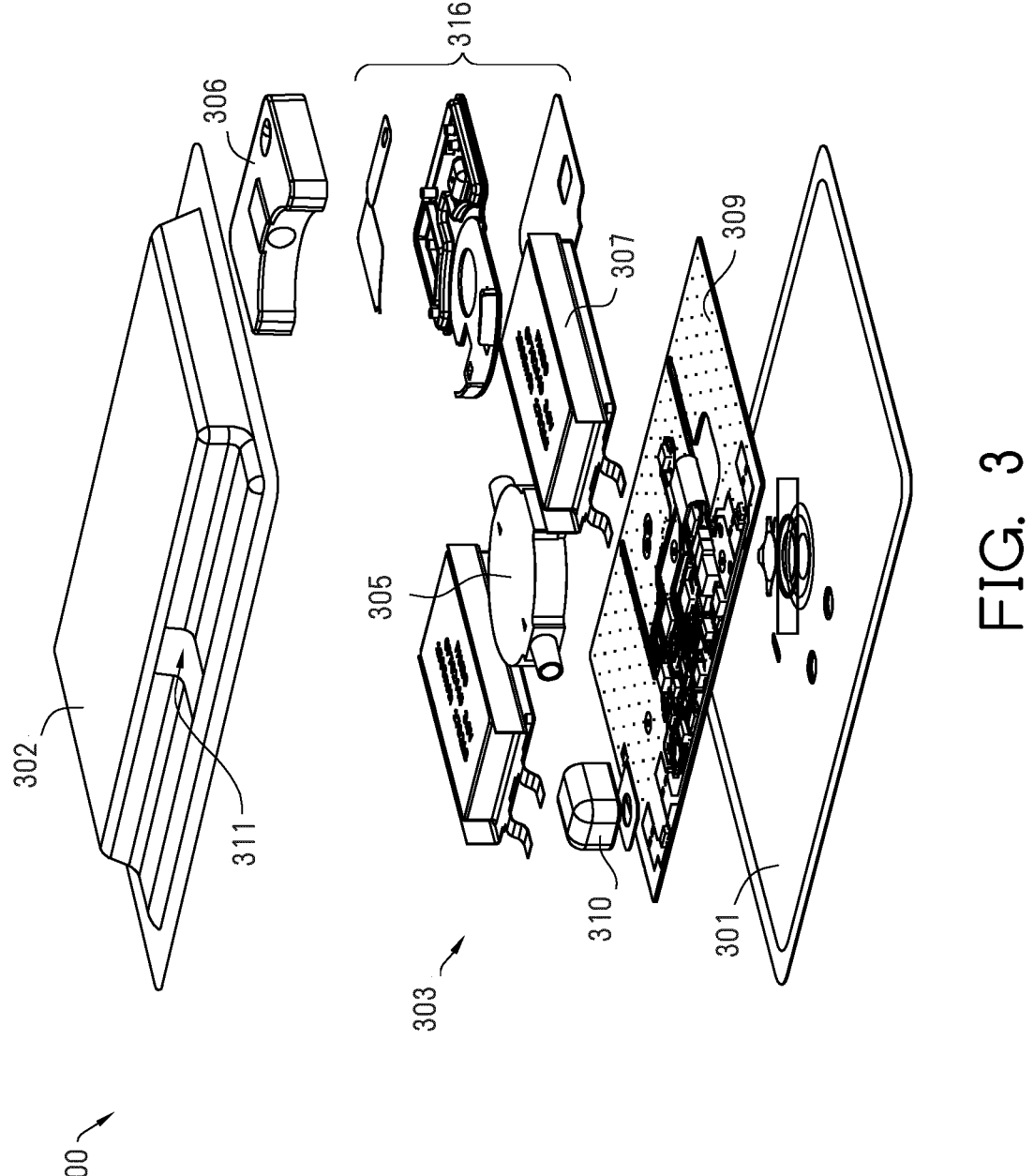
FIG. 3 is an exploded perspective view of an electronics assembly enclosing an electronics unit within a housing.

FIG. 3 illustrates an electronics assembly 300 enclosing an electronics unit within a housing. As illustrated in FIG. 3, the housing of the electronics assembly 300 can include a plate 301 and flexible film 302 enclosing the electronics unit 303 within. The electronics unit 303 can include a pump 305, inlet protection mechanism 310, pump exhaust mechanism 306, power source 307, and circuit board 309. The circuit board 309 can be flexible or substantially flexible.

As is illustrated, the pump exhaust mechanism 306 can be an enclosure, such as a chamber. The electronics unit 303 and pump 305 can be used without the inlet protection mechanism 310. However, the pump exhaust mechanism 306 and the pump 305 can sit within an extended casing 316.

The flexible film 302 can be attached to the plate 301 to form a fluid tight seal and enclosure around the electronic components. The flexible film 302 can be attached to the plate at a perimeter of the plate by heat welding, adhesive bonding, ultrasonic welding, RF welding, or any other attachment or bonding technique.

The flexible film 302 can include an aperture 311. The aperture 311 can allow the inlet protection mechanism 310 to be in fluid communication with the absorbent and/or transmission layers of the wound dressing. The perimeter of the aperture 311 of the flexible film 303 can be sealed or attached to the inlet protection mechanism 310 to form a fluid tight seal and enclosure around the inlet protection mechanism 310 allowing the electronic components 303 to remain protected from fluid within the dressing. The flexible film 302 can be attached to the inlet protection mechanism 310 at a perimeter of the inlet protection mechanism 310 by heat welding, adhesive bonding, ultrasonic welding, RF welding, or any other attachment or bonding technique. The inlet protection mechanism 310 can prevent wound exudate or liquids from the wound and collected in the absorbent area 660 of the wound dressing from entering the pump and/or electronic components of the electronics assembly 300.

The electronics assembly 300 illustrated in FIG. 3 can be incorporated within the wound dressing such that, once the dressing is applied to the body of the patient, air from within the dressing can pass through the inlet protection mechanism 310 to be pumped out toward the pump exhaust mechanism 306 in communication with an aperture in the casing 316 and the circuit board 309 as described herein.

Figure 4A:
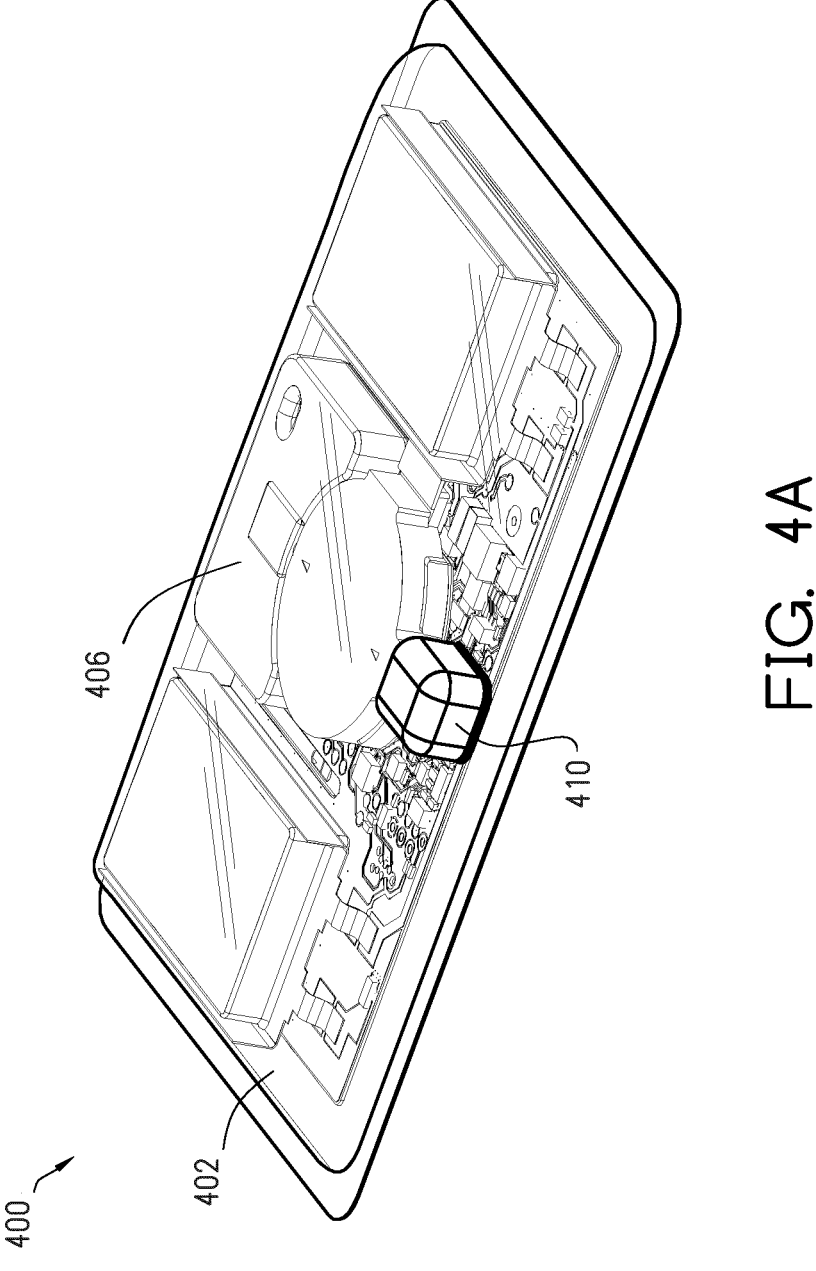
FIG. 4A illustrates a bottom perspective view of the electronics assembly of FIG. 3.
Figure 4B:
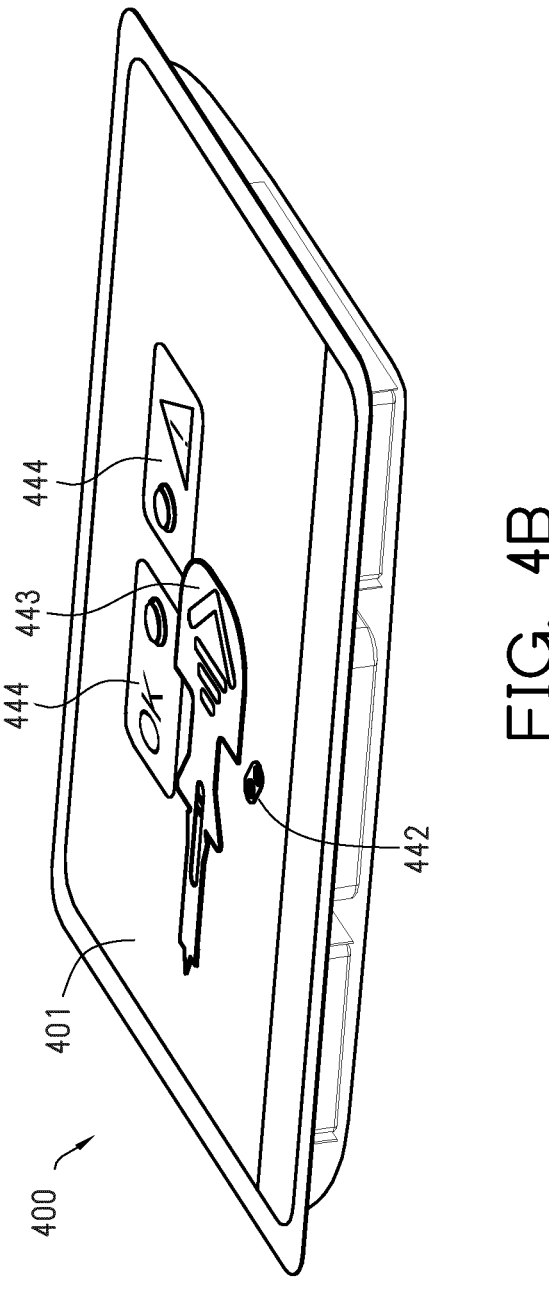
FIG. 4B illustrates a top perspective view of the electronics assembly of FIG. 3.

FIGS. 4A-B illustrate an electronics assembly 400 including a pump inlet protection mechanism 410 sealed to the exterior of the flexible film 402, similar to the description with reference to FIG. 3. Also shown is an exhaust mechanism 406, which can be similar to the exhaust mechanism 306.

FIG. 4A illustrates lower, wound facing surface of the electronics assembly 400. FIG. 4B shows an upper surface of the plate 401 (which can face the patient or user) of the electronics assembly 400. The upper surface of the plate 401 can include an on/off switch or button cover 443, indicators 444, and/or one or more vent holes 442.

The electronics assembly 400 with the pump inlet protection mechanism 410 extending from and sealed to the film 402 can be positioned within the aperture 172 in the cover layer 113 and absorbent layer(s) (122, 151) as shown in FIG. 1C. The perimeter of the electronics assembly 400 can be sealed to a top surface of the outer perimeter of the aperture 172 in the cover layer 113 as shown in FIG. 1C and described in more detail with reference to FIG. 5A-5B herein. The electronics assembly 400 can be sealed to the cover layer 113 with a sealant gasket, adhesive, heat welding, adhesive bonding, ultrasonic welding, RF welding, or any other attachment or bonding technique. The electronics assembly 400 can be permanently sealed to the cover layer 113 and could not be removed from the cover layer without destroying the dressing.

The electronics assembly 400 can be utilized in a single dressing and disposed of with the dressing. In some cases, the electronics assembly 400 can be utilized in a series of dressings.

Figure 5A:
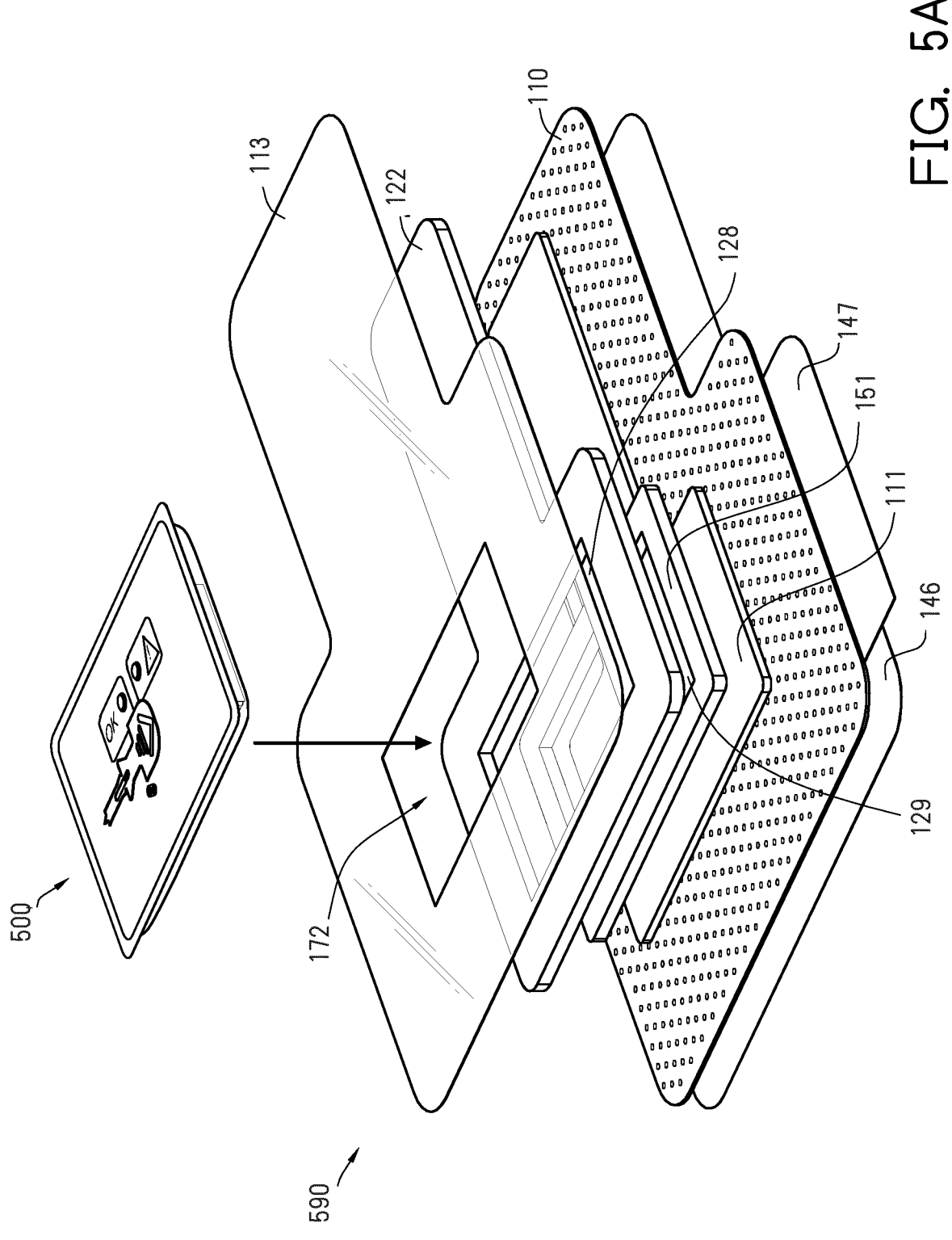
FIG. 5A is an exploded view of a wound dressing incorporating an electronics assembly within the wound dressing layers.
Figure 5B:
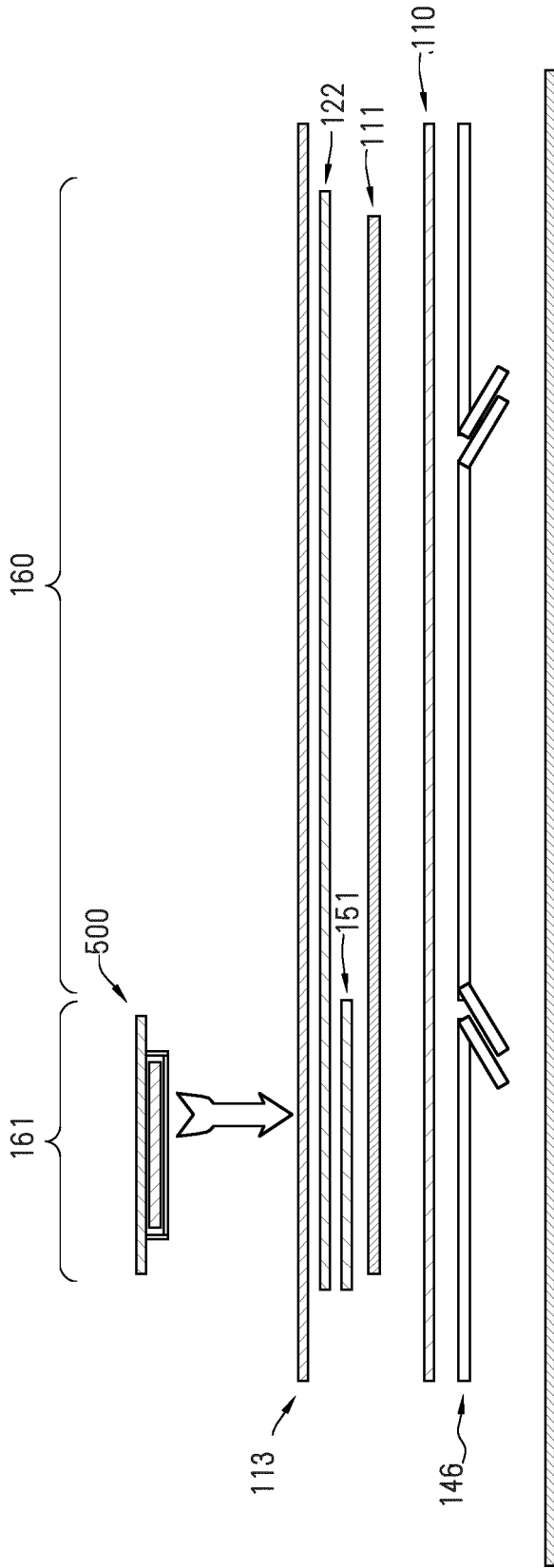
FIG. 5B illustrates a cross sectional layout of the material layers of a wound dressing incorporating an electronics assembly within the dressing.

FIG. 5A illustrates a wound dressing, such as the one in FIG. 1C, incorporating an electronics assembly 500 within the wound dressing layers 590. FIG. 5B illustrates a cross-sectional view of the wound dressing incorporating the electronics assembly of FIG. 5A. The electronics assembly 500 can be provided within the aperture 172 in the cover layer and apertures 129 and 128 in the first and second absorbent layers 122, 151. The electronics assembly 500 can seal to the outer perimeter of the aperture 172 of the cover layer. The dressing can comprise a wound contact layer 110 and a moisture vapor permeable film, cover layer or backing layer 113 positioned above the contact layer 110 and other layers of the dressing. A layer 111 of porous material can be located above the wound contact layer 110. As used herein, the terms porous material, spacer, and/or transmission layer can be used interchangeably to refer to the layer of material in the dressing configured to distribute negative pressure throughout the wound area. This porous layer, or transmission layer, 111 allows transmission of fluid including liquid and gas away from a wound site into upper layers of the wound dressing. Further, one or more absorbent layers (such as layers 122, 151) for absorbing and retaining exudate aspirated from the wound can be utilized. The one or more layers 122, 151 of absorbent material may be provided above the transmission layer 111. There may be a small apertured absorbent layer 151 and a large aperture absorbent layer 122. The small apertured absorbent layer 151 can be positioned on top of the large apertured absorbent layer 122. In some cases, the small apertured absorbent layer 151 can be positioned below of the large apertured absorbent layer 122. Before use, the dressing can include one or more delivery layers 146 adhered to the bottom surface of the wound contact layer. The delivery layer 146 can cover adhesive or apertures on the bottom surface of the wound contact layer 110.

FIGS. 6A-6B and 7A-7B illustrate an electronics assembly 600 with a pump inlet protection mechanism 610 and pump exhaust mechanism 674 on a pump 672. The assembly 600 can include cavities 682 and 683 (shown in FIGS. 7A-7B) on the pump inlet protection mechanism 610 and pump exhaust mechanism 674, respectively. The inlet protection and pump exhaust mechanisms can be adhered to the inlet and the outlet of the pump as described herein. The assembly 600 can be assembled using an adhesive and allowed to cure prior to incorporating into the electronics assembly.

The pump inlet can be covered or fitted with a pump inlet protection mechanism 610. The pump inlet protection 610 can be pushed onto the pump inlet as illustrated by the arrows in FIG. 7A. This can be a friction fit. The port of the pump inlet protection 610 that receives a portion of the pump inlet can be sized and shaped to be a complementary fit around the pump inlet. The pump inlet protection 610 can be bonded onto the pump inlet using a silicone sealant or any other sealant or sealing technique. FIG. 7B illustrates the pump inlet protection mechanism 610 covering the pump inlet and the pump exhaust mechanism 674 covering the pump outlet. The pump exhaust mechanism 674 can include one or more apertures or vents 684 to allow gas aspirated by the pump to be exhausted from the pump exhaust mechanism 674. In some cases, a non-return valve and/or filter membrane of the pump exhaust mechanism is included in the pump exhaust mechanism 674.

Figure 6A:
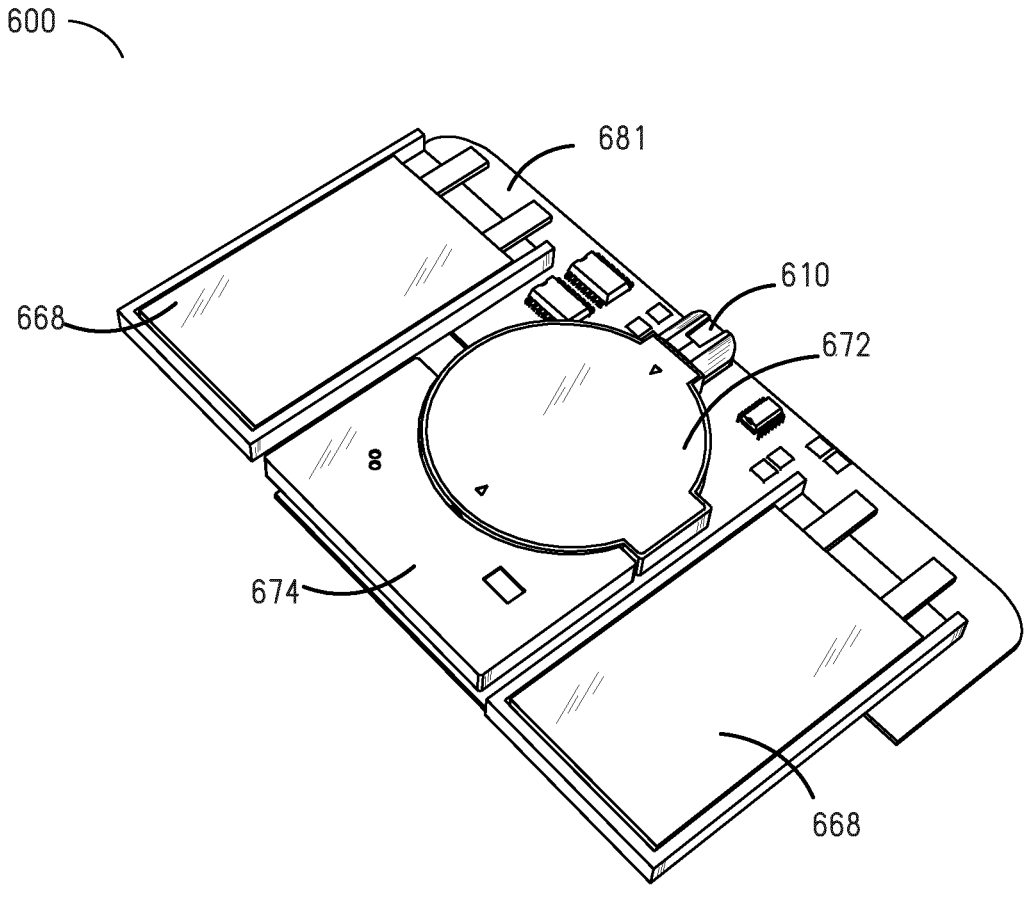
FIGS. 6A-6B and 7A-7B illustrate components of an electronics assembly.
Figure 6B:
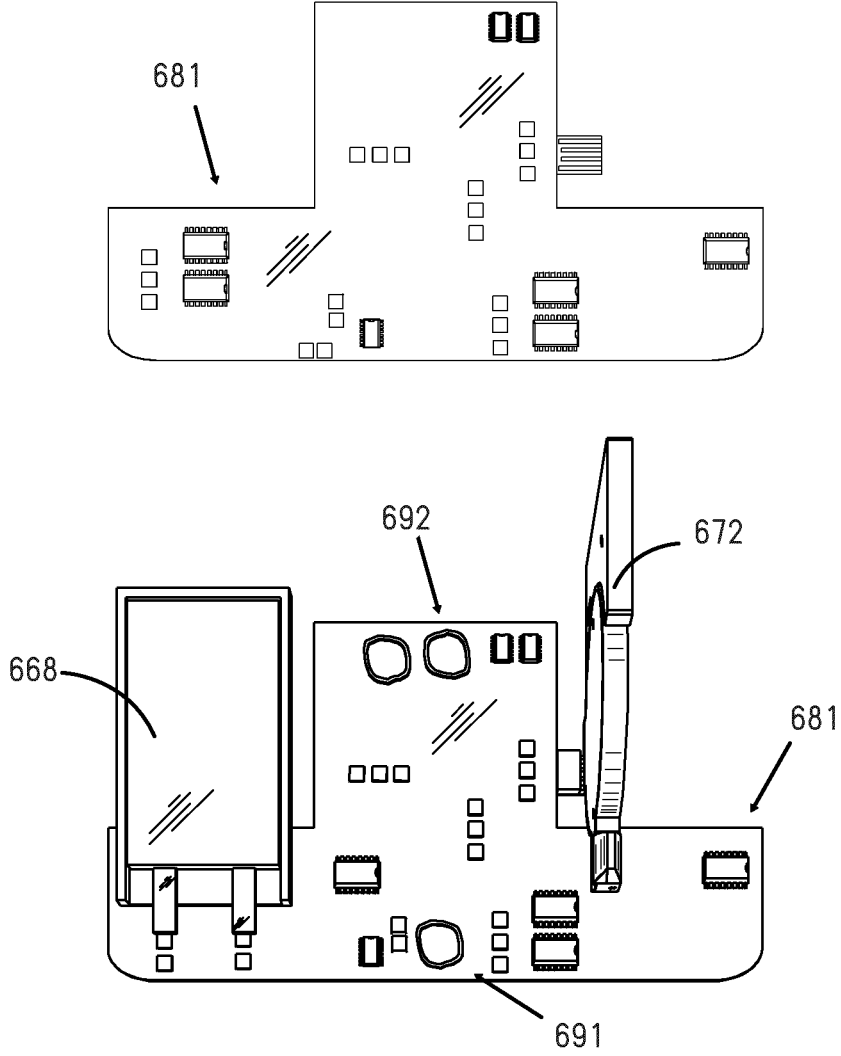
Figure 7A:
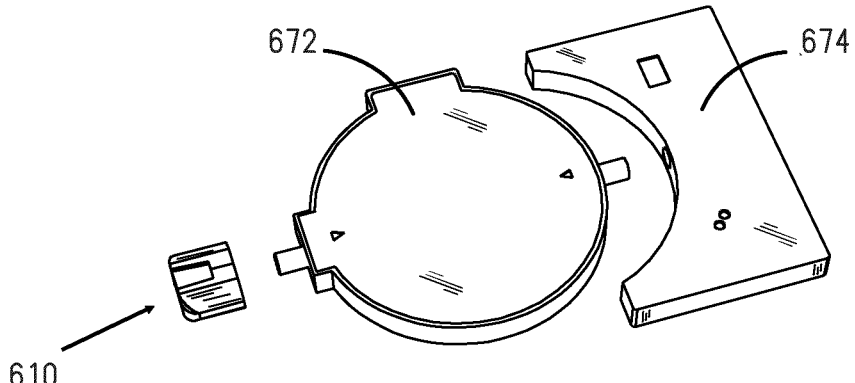
Figure 7B:
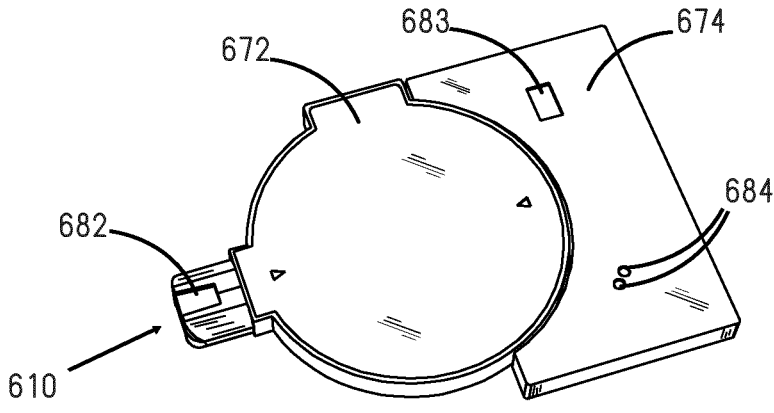

FIGS. 7A-7B illustrate the pump inlet protection mechanism 610 and pump exhaust mechanism 674 with cavities 682 and 683. A pump assembly including the pump inlet protection mechanism 610 and pump exhaust mechanism 674 can be placed over the surface of a circuit board 681. When the pump assembly is in contact with the surface of the circuit board 681, the cavities 682 and 683 can at least partially enclose sensors on the circuit board 681, for example, pressure sensors 691 and 692 on the circuit board 681, as illustrated in FIG. 6B.

The pressure sensors 691 and 692 illustrated in FIG. 6B can be used to measure and/or monitor the pressure level at the wound and atmospheric pressure. The pressure sensor 691 can be used to measure and/or monitor pressure at the wound (such as, underneath the wound dressing), which can be accomplished by measuring and/or monitoring pressure in a fluid flow path connecting the negative pressure source or pump 672 and the wound. The pressure sensor 691 can measure and/or monitor pressure in the cavity 682 of the pump inlet protection mechanism 610 shown in FIGS. 7A-7B.

The pressure sensor 692 can be used to measure and/or monitor pressure external to the wound dressing. The pressure sensor 692 can measure and/or monitor pressure in the cavity 683 of the pump exhaust mechanism 674 shown in FIGS. 7A-7B. The pressure sensor 692 can measure pressure external to the wound dressing, which can be relative atmospheric pressure since the atmospheric pressure varies depending on, for instance, an altitude of use or pressurized environment in which the TNP apparatus may be used.

These measurements can be used to establish a desired negative pressure differential (or target negative pressure or setpoint) at the wound relative to the external pressure.

The circuit board 681 (including any of the circuit boards described herein) can include control circuitry, such as one or more processors or controllers, that can control the supply of negative pressure by the negative pressure source 672 according at least to a comparison between the pressure monitored by the pressure sensor 691 and the pressure monitored by the pressure sensor 692. Control circuitry can operate the negative pressure source 672 in a first mode (that can be referred to as an initial pump down mode) in which the negative pressure source 672 is activated to establish the negative pressure setpoint at the wound. The setpoint can be set to, for example, a value in the range between about −70 mmHg to about −90 mmHg, among others. Once the setpoint has been established, which can be verified based on a difference between pressure measured by the pressure sensor 691 (or wound pressure) and pressure measured by the pressure sensor 692 (or external pressure), control circuitry can deactivate (or pause) operation of the negative pressure source 672. Control circuitry can operate the negative pressure source 672 is a second mode (that can be referred to as maintenance pump down mode) in which the negative pressure source 672 is periodically activated to re-establish the negative pressure setpoint when the wound is depressurized as a result of one or more leaks in the fluid flow path, which may be caused, among other things, by an imperfect seal between the dressing and skin or tissue surrounding the wound. Control circuitry can activate the negative pressure source 672 in response to the pressure at the wound (as monitored by the pressure sensor 691) becomes more positive than a negative pressure threshold, which can be set to the same negative pressure as the setpoint or lower negative pressure. Control circuitry can include one or more memories, which can be volatile or nonvolatile memory.

Any of the wound dressings, wound treatment apparatuses and methods described herein may also be used in combination or in addition to one or more features described in PCT International Application No. PCT/EP2017/060464, filed May 3, 2017, titled NEGATIVE PRESSURE WOUND THERAPY DEVICE ACTIVATION AND CONTROL, U.S. Pat. Nos. 8,734,425, and 8,905,985, each of which is hereby incorporated by reference in its entirety herein.

One or more self-adhesive gaskets can be applied to the pump inlet protection mechanism 610 and pump exhaust mechanism 674 to seal the cavities 682 and 683 of the pump inlet and pump exhaust around sensors on the circuit board 681 and to seal around the exhaust mechanism vent(s) and corresponding vent(s) in the circuit board 681 (as described herein). A pre-formed adhesive sheet can be used to form the sealing gaskets between the cavities 682 and 683 of the pump inlet and pump exhaust mechanisms and sensors on the circuit board 681 and between the exhaust mechanism vent(s) and vent(s) in the circuit board 681. An adhesive can be used to seal the cavities 682 and 683 of the pump inlet protection 610 and pump exhaust mechanism 674 around sensors on the circuit board 681 and to seal around the exhaust mechanism vent(s) 684 and corresponding vent(s) in the circuit board. As described herein, the electronics assembly 600 can be embedded within layers of the dressing, such as in cutouts or recesses into which the electronics assembly can be placed.

The pump inlet protection mechanism 610 can provide a large surface area available for vacuum to be drawn by the inlet of the pump. A pump inlet (shown as rounded protrusion in FIG. 7A) can fit within a recess in the pump inlet protection mechanism 610. The pump inlet can be attached by friction fit and/or form a complementary fit to the recess of the pump inlet protection mechanism.

The pump inlet protection mechanism 610 can allow air or gas to pass through, but can block liquid from reaching the negative pressure source. The pump inlet protection mechanism 610 can include a porous material. The pump inlet protection mechanism 610 can comprise one or more porous polymer molded components. The pump inlet protection mechanism 610 can include hydrophobic or substantially hydrophobic material. Material included in the pump inlet protection mechanism 610 can have a pore size in the range of approximately 5 microns to approximately 40 microns. The pore size can be approximately 10 microns. In some cases, the pump inlet protection mechanism 610 can include a polymer that can be one of hydrophobic polyethylene or hydrophobic polypropylene. In some cases, the pump inlet protection mechanism can include a Porvair Vyon material with a pore size of 10 microns. Any of the pump inlet protection mechanism described herein can include one or more features of the pump inlet protection mechanism 610.

Monitoring Operational Lifetime

Figure 8A:
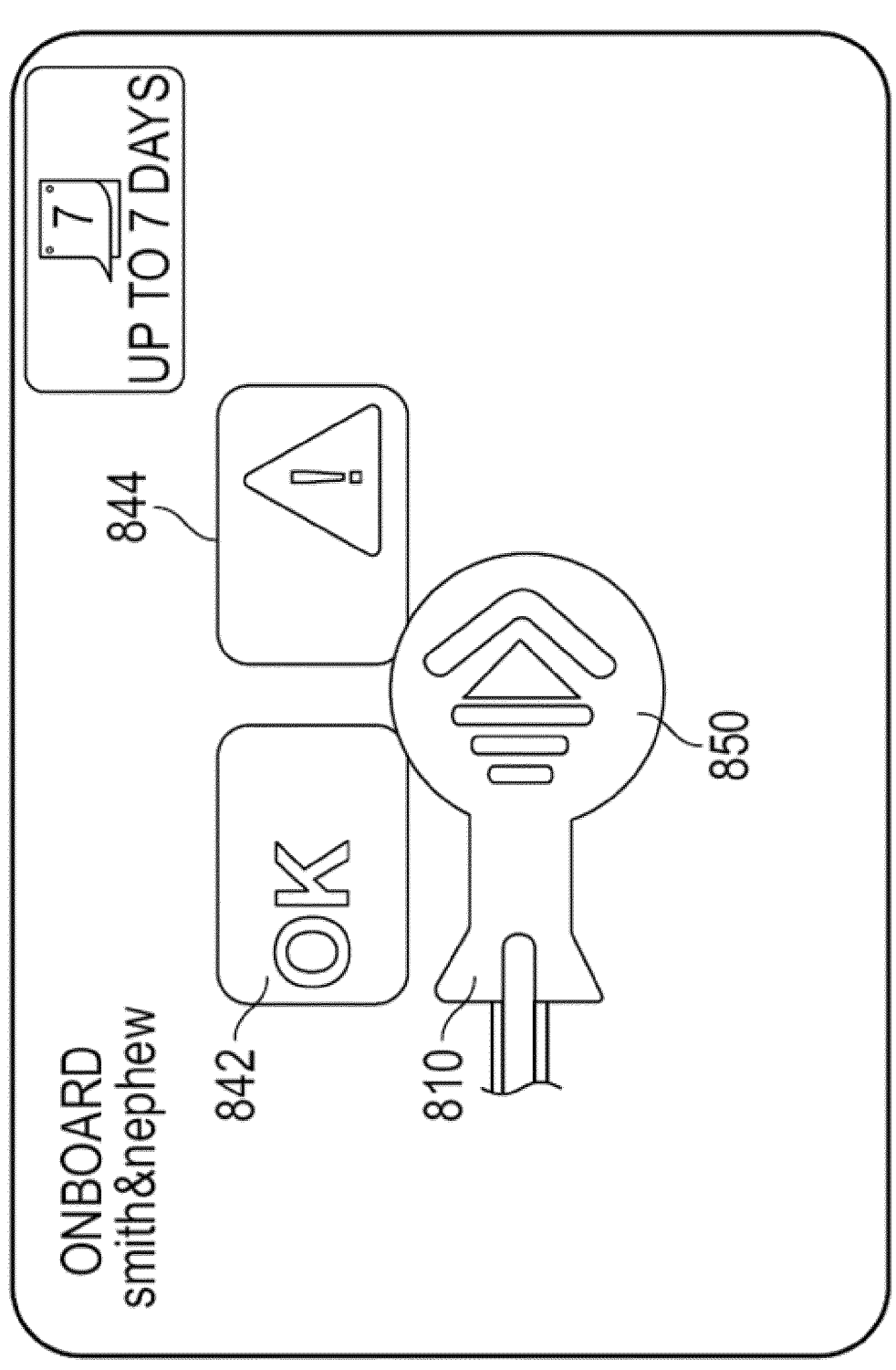
FIGS. 8A-8B illustrate activation of a system.
Figure 8B:
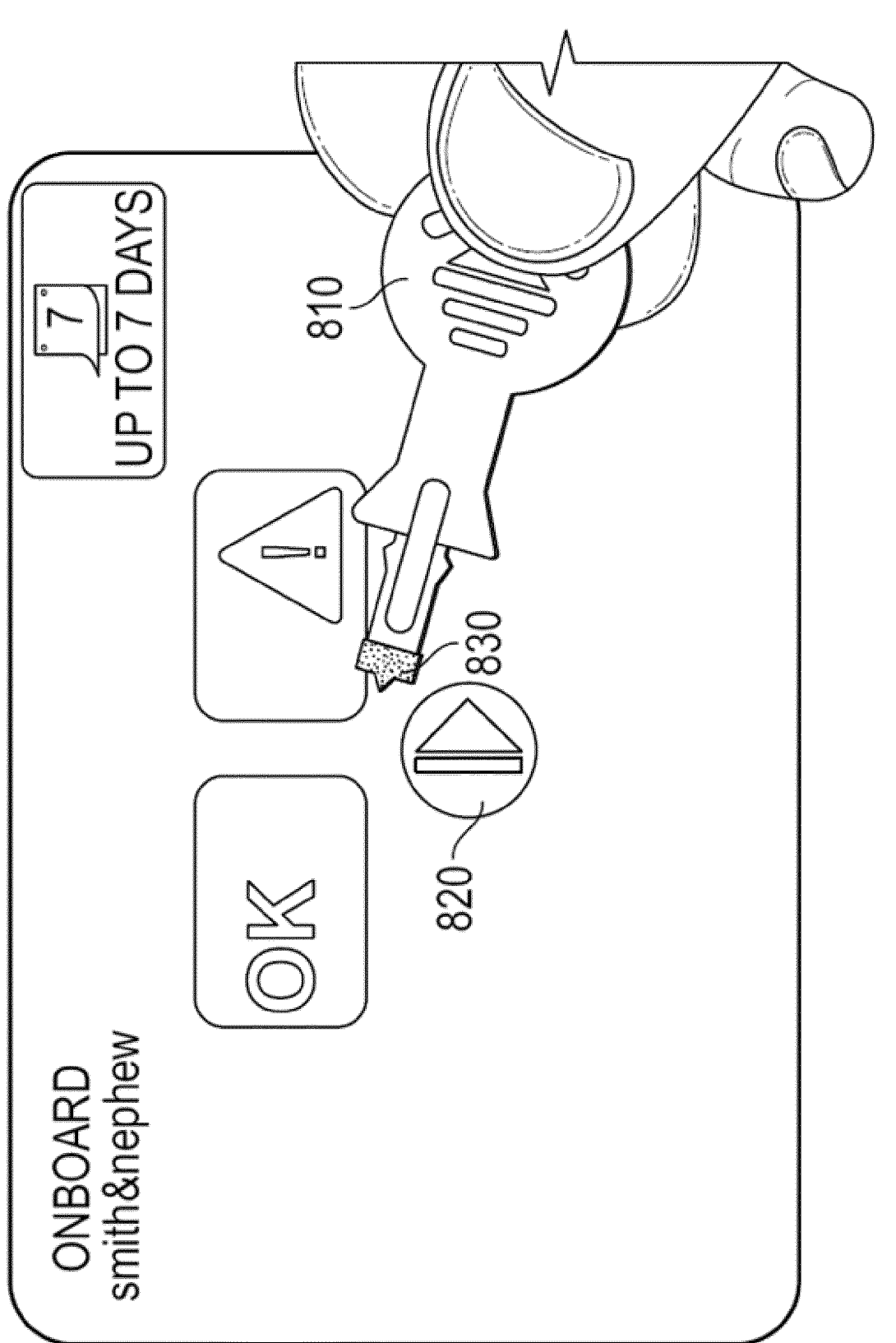

FIGS. 8A and 8B illustrate activation of any of the devices or systems disclosed herein. Activation can be performed in multiple steps in order to reduce the risk of inadvertent activation, which may lessen the risk of malfunction or accident during sterilization (for example, lessen the risk of combusting gas used during sterilization, such as ethylene oxide, as a result of a spark or the like). For instance, pull tab 810 can be removed to expose a button or switch 820, thereby reducing the likelihood that the activation may be executed in a reverse order. Removal of the pull tab 810 can cause removal of isolating material 830 from the surface of a switch (not shown, but in some cases from the opposite side of the switch) so that an electrical connection can be formed. Also illustrated are indicators 842 and 844 that can indicate the state of operation of the system, as described herein. The pull tab 810 can include a pattern 850 instructing the user to pull the tab in a particular direction (for example, to the left). Further details of activation are disclosed in International Patent Publication No. WO 2019/086475, which is incorporated by reference in its entirety.

Figure 9:
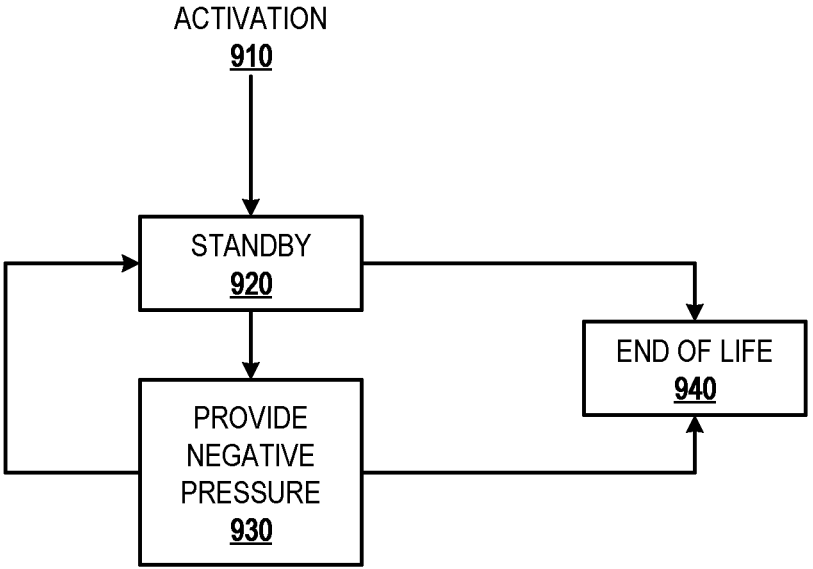
FIG. 9 illustrates operation of a negative pressure wound therapy system.

FIG. 9 illustrates operation of any of the devices or systems described herein. The process illustrated in FIG. 9 can be performed, for example, by the control circuitry. With reference to FIG. 9, activation 910 can involve activating the control circuitry of the system. Removing the pull tab 810 can cause the activation 910. Activation can cause the system to transition to a standby mode or state 920. In the standby state 920, the system can be ready to supply negative pressure wound to a wound.

In response to pressing a button, such as the button 820, the system can transition to a mode or state 930 in which the negative pressure source is activated to supply negative pressure to the wound. State 930 can encompass the initial pump down mode and the maintenance pump down mode as described herein. The system can transition from the state 930 to the standby state 920 in response to one or more conditions, such as a press of the button, detection of a leak in the fluid flow path, or the like. Negative pressure source can be deactivated in the standby state 920.

Any of the devices or systems disclosed herein can be configured to provide therapy for a limited duration of time (sometimes referred to as permitted total operational time), such as 1 day or less or more, 2-10 days or less or more, 14 days or less or more, or the like. Permitted total operational time can be fixed or variable (for example, based on various operating conditions or the like). The fixed value can be programmed in a memory (for example, nonvolatile memory). The system can be disposed upon expiration of the permitted total operational time.

The system (for example, the control circuitry) can monitor the duration of time following activation of the system. For example, the system can monitor duration of time following at least one of removal of the pull tab 810 or pressing the button 820. As another example, the system can monitor duration of time following initial (or first) activation of the negative pressure source, such as the initial transition into the state 930.

With reference to FIG. 9, when the monitored duration of time reaches or exceeds the permitted total operational time, the system can transition to an end of life mode or state 940. In the end of life state 940, the system can be configured to deactivate provision of negative pressure wound therapy. For example, the system can be configured to not allow activation of the negative pressure source. The system can be configured to disable reactivation of the negative pressure source once the end of life state 940 has been reached. This can be accomplished by storing an indication, value, flag, or the like in the memory (for example, nonvolatile memory). Upon one or more of transition to or in the end of life state 940, the system can indicate to a user that the permitted total operational time has been reached or exceeded. For instance, the system can be configured to activate one or more of the indicators, deactivate all of the indicators, deactivate the button, or the like. In some cases, transitioning to the end of life state 940 may mean that the system can be disposed of.

The system (for example, the control circuitry) can monitor the duration of time following activation of the system by, for example, by maintaining a timer in firmware, software, hardware, or any combination thereof. In some cases, the system may not maintain a separate timer, which may be advantageous for one or more of improving efficiency, reducing use of resources (such as, power), reducing cost, or the like. The system (for example, the control circuitry) may instead monitor the duration of time based on a memory address used for periodically logging or storing operational data in memory, such as in nonvolatile memory, which can be read-only memory (ROM), electrically erasable programmable read-only memory (EEPROM), flash memory, or the like.

For example, the system can periodically log operational data in the memory at expiration of fixed (or variable) period of time, such as every minute or less or more, every two minutes or less or more, every three minutes or less or more, every four minutes or less or more, every five minutes or less or more, or the like. The size of the logged data can be fixed. For example, the size of logged data can be the same every time data is logged, such as 1 byte or less or more, 4 bytes or less or more, 8 bytes or less or more, 12 bytes or less or more, 16 bytes or less or more, or the like. As another example, the size of logged data may vary according to a known pattern. Accordingly, memory address for logging the data can be incremented by the size of logged data for the subsequent data logging operation. Memory address can be incremented periodically in accordance with the frequency with which data is logged in the memory.

For instance, assuming that 16 bytes of data is logged once a minute and that each memory address is configured to store 1 byte of data, the memory address for logging data can be incremented by 16 bytes every minute. Further, assuming that permitted total operational time is 7 days and that data is logged for the first time at the memory address of zero, the system can transition to the end of life state 940 when the memory address has reached the address 161,280. This threshold address can be determined as follows:

$$16 \text{ memory addresses written to/minute} * 60 \text{ minutes/} \\ \text{hour} * 24 \text{ hours/day} * 7 \text{ days.}$$

The system (for example, the control circuitry) can determine whether the memory address has reached the memory address indicative of reaching the total permitted operational time of the system. This determination can be performed prior to or during logging the data. Logged data can include operational data. For example, logged data can include one or more of activations and/or deactivations of the negative pressure source, pressure measurements (for example, differential pressure between pressure in the fluid flow path and measured external pressure), external pressure, operating parameters of the power source (such as, voltage), duration of initial pump down, temperature, or the like. Any of the logged data can include historical data.

Other Variations

While certain embodiments described herein relate to integrated negative pressure wound therapy systems in which the negative pressure source is supported by the dressing, systems and methods described herein are applicable to any negative pressure wound therapy system or medical system. For example, systems and methods for monitoring operational lifetime described herein can be used in negative pressure wound therapy systems or medical systems. Such systems can be configured with the negative pressure source and/or electronics being external to the wound dressing, such as with the negative pressure source and/or electronics being positioned in a fluid proof enclosure. Additionally, the systems and methods disclosed herein can be utilized by ultrasound delivery devices, negative pressure devices powered by an external power supply (including PICO device manufactured by Smith & Nephew), negative pressure devices with a separate pump, and medical devices generally. Any of the embodiments disclosed herein can be used with one or more features disclosed in U.S. Pat. No. 7,779,625, titled "DEVICE AND METHOD FOR WOUND THERAPY," issued Aug. 24, 2010; U.S. Pat. No. 7,964,766, titled "WOUND CLEANSING APPARATUS IN SITU," issued on Jun. 21, 2011; U.S. Pat. No. 8,235,955, titled "WOUND TREATMENT APPARATUS AND METHOD," issued on Aug. 7, 2012; U.S. Pat. No. 7,753,894, titled "WOUND CLEANSING APPARATUS WITH STRESS," issued Jul. 13, 2010; U.S. Pat. No. 8,764,732, titled "WOUND DRESSING," issued Jul. 1, 2014; U.S. Pat. No. 8,808,274, titled "WOUND DRESSING," issued Aug. 19, 2014; U.S. Pat. No. 9,061,095, titled "WOUND DRESSING AND METHOD OF USE," issued Jun. 23, 2015; U.S. Pat. No. 10,076,449, issued Sep. 18, 2018, titled "WOUND DRESSING AND METHOD OF TREATMENT"; U.S. patent application Ser. No. 14/418,908, filed Jan. 30, 2015, published as U.S. Publication No. 2015/0190286, published Jul. 9, 2015, titled "WOUND DRESSING AND METHOD OF TREATMENT"; U.S. Pat. No. 10,231,878, titled "TISSUE HEALING," issued Mar. 19, 2019; PCT International Application PCT/GB2012/000587, titled "WOUND DRESSING AND METHOD OF TREATMENT" and filed on Jul. 12, 2012; International Application No. PCT/IB2013/001469, filed May 22, 2013, titled "APPARATUSES AND METHODS FOR NEGATIVE PRESSURE WOUND THERAPY"; PCT International Application No. PCT/

IB2013/002102, filed Jul. 31, 2013, titled "WOUND DRESSING AND METHOD OF TREATMENT"; PCT International Application No. PCT/IB2013/002060, filed Jul. 31, 2013, titled "WOUND DRESSING AND METHOD OF TREATMENT"; PCT International Application No. PCT/IB2013/00084, filed Mar. 12, 2013, titled "REDUCED PRESSURE APPARATUS AND METHODS"; International Application No. PCT/EP2016/059329, filed Apr. 26, 2016, titled "REDUCED PRESSURE APPARATUSES"; PCT International Application No. PCT/EP2017/059883, filed Apr. 26, 2017, titled "WOUND DRESSINGS AND METHODS OF USE WITH INTEGRATED NEGATIVE PRESSURE SOURCE HAVING A FLUID INGRESS INHIBITION COMPONENT"; PCT International Application No. PCT/EP2017/055225, filed Mar. 6, 2017, titled "WOUND TREATMENT APPARATUSES AND METHODS WITH NEGATIVE PRESSURE SOURCE INTEGRATED INTO WOUND DRESSING"; PCT International Application No. PCT/EP2018/074694, filed Sep. 13, 2018, titled "NEGATIVE PRESSURE WOUND TREATMENT APPARATUSES AND METHODS WITH INTEGRATED ELECTRONICS"; PCT International Application No. PCT/EP2018/074701, filed Sep. 13, 2018, titled "NEGATIVE PRESSURE WOUND TREATMENT APPARATUSES AND METHODS WITH INTEGRATED ELECTRONICS"; PCT International Application No. PCT/EP2018/079345, filed Oct. 25, 2018, titled "NEGATIVE PRESSURE WOUND TREATMENT APPARATUSES AND METHODS WITH INTEGRATED ELECTRONICS"; PCT International Application No. PCT/EP2018/079745, filed Oct. 30, 2018, titled "SAFE OPERATION OF INTEGRATED NEGATIVE PRESSURE WOUND TREATMENT APPARATUSES"; each of which is incorporated by reference herein in its entirety.

Although certain embodiments described herein relate to wound dressings, systems and methods disclosed herein are not limited to wound dressings or medical applications. Systems and methods disclosed herein are generally applicable to electronic devices in general, such as electronic devices that can be worn by or applied to a user.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure.

The various components illustrated in the figures or described herein may be implemented as software or firmware on a processor, controller, ASIC, FPGA, or dedicated hardware. The software or firmware can include instructions stored in a non-transitory computer-readable memory. The instructions can be executed by a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A negative pressure wound therapy system comprising:
a source of negative pressure configured to provide negative pressure therapy to a wound covered by a wound dressing; and
an electronic processing circuitry comprising a memory and configured to:
periodically store a plurality of data sets at a plurality of memory locations in the memory associated with a plurality of memory addresses by storing a first data set of the plurality of data sets at a first memory location of the plurality of memory locations associated with a first memory address of the plurality of memory addresses and subsequently storing a second data set of the plurality of data sets at a second memory location of the plurality of memory locations associated with a second memory address of the plurality of memory addresses;
determine that a total permitted operational time for providing negative pressure has been reached in response to:
storing a most recent data set of the plurality of data sets, and
determining that a third memory address of the plurality of memory addresses that is associated with a third memory location of the plurality of memory locations that stores the most recent data set corresponds to a memory address indicative of a duration of time following an initial activation of the electronic processing circuitry reaching the total permitted operational time for providing negative pressure therapy; and
in response to determining that the total permitted operational time for providing negative pressure therapy has been reached, provide an indication that comprises permanently disabling provision of negative pressure therapy by the source of negative pressure.

2. The system of claim 1, wherein the electronic processing circuitry is configured to store each data set of the plurality of data sets at an expiration of a time interval.

3. The system of claim 2, wherein the time interval is fixed.

4. The system of claim 1, wherein the plurality of data sets are of a fixed size.

5. The system of claim 1, wherein the electronic processing circuitry is configured to determine the second memory address by incrementing the first memory address by a size of the first data set.

6. The system of claim 1, wherein the memory address indicative of the duration of time following the initial activation of the electronic processing circuitry reaching the total permitted operational time for providing negative pressure therapy is determined based on a frequency of storing the plurality of data sets in the memory, size of the plurality of data sets, and the total permitted operational time for providing negative pressure therapy.

7. The system of claim 6, wherein the memory address indicative of the duration of time following the initial activation of the electronic processing circuitry reaching the total permitted operational time for providing negative pressure therapy is determined by multiplying the frequency of storing the plurality of data sets in the memory by the size of the plurality of data sets and the total permitted operational time for providing negative pressure therapy.

8. The system of claim 6, wherein the memory address indicative of the duration of time following the initial activation of the electronic processing circuitry reaching the total permitted operational time for providing negative pressure therapy is further determined based on a size of data configured to be stored at the plurality of memory locations.

9. The system of claim 6, wherein the total permitted operational time for providing negative pressure therapy comprises 7 days, 10 days, or 14 days.

10. The system of claim 1, wherein the plurality of data sets comprise data related to provision of negative pressure therapy.

11. The system of claim 1 further comprising a power source configured to power the electronic processing circuitry, wherein the source of negative pressure, the electronic processing circuitry, and the power source are disposed on or within the wound dressing.

12. The system of claim 1, wherein the electronic processing circuitry is configured to provide the indication further by activating or deactivating at least one user interface component.

13. The system of claim 1, wherein the electronic processing circuitry is configured to provide the indication further by storing a value in the memory, the value indicating that the total permitted operational time for providing negative pressure therapy has been reached.

14. The system of claim 1, wherein the electronic processing circuitry is configured to determine that the total permitted operational time for providing negative pressure has been reached without considering data stored at the plurality of memory locations.

15. A method of operating a negative pressure wound therapy system, the method comprising:

by an electronic processing circuitry of the negative pressure wound therapy system:

providing negative pressure therapy by a source of negative pressure to a wound covered by a wound dressing;

periodically storing a plurality of data sets at a plurality of memory locations in the memory associated with a plurality of memory addresses by storing a first data set of the plurality of data sets at a first memory location of the plurality of memory locations associated with a first memory address of the plurality of memory addresses and subsequently storing a second data set of the plurality of data sets at a second memory location of the plurality of memory locations associated with a second memory address of the plurality of memory addresses;

determining that a total permitted operational time for providing negative pressure has been reached in response to:

storing a most recent data set of the plurality of data sets, and determining that a third memory address of the plurality of memory addresses that is associated with a third memory location of the plurality of memory locations that stores the most recent data set corresponds to a memory address indicative of a duration of time following an initial activation of the electronic processing circuitry reaching the total permitted operational time for providing negative pressure therapy; and in response to determining that the total permitted operational time for providing negative pressure therapy has been reached, providing an indication that comprises permanently disabling provision of negative pressure therapy by the source of negative pressure.

16. The method of claim 15, further comprising storing each data set of the plurality of data sets at an expiration of a time interval.

17. The method of claim 16, wherein the time interval is fixed.

18. The method of claim 15, wherein the plurality of data sets are of a fixed size.

19. The method of claim 15, further comprising determining the second memory address by incrementing the first memory address by a size of the first data set.

20. The method of claim 15, wherein the memory address indicative of the duration of time following the initial activation of the electronic processing circuitry reaching the total permitted operational time for providing negative pressure therapy is determined based on a frequency of storing the plurality of data sets in the memory, size of the plurality of data sets, and the total permitted operational time for providing negative pressure therapy.

21. The method of claim 20, wherein the memory address indicative of the duration of time following the initial activation of the electronic processing circuitry reaching the total permitted operational time for providing negative pressure therapy is determined by multiplying the frequency of storing the plurality of data sets in the memory by the size of the plurality of data sets and the total permitted operational time for providing negative pressure therapy.

* * * * *